United States Patent [19]

Polywka et al.

[11] Patent Number: 6,162,951

[45] Date of Patent: Dec. 19, 2000

[54] PHOSPHINE LIGANDS

[75] Inventors: Mario Eugenio Cosamino Polywka, Blewbery; Edwin Moses, Goring on Thames; Daniel John Bayston, Bicester; Anthony David Baxter, Abingdon; Mark Richard Ashton, Didcot, all of United Kingdom

[73] Assignee: Oxford Asymmetry International plc, Abingdon, United Kingdom

[21] Appl. No.: 09/272,300

[22] Filed: Mar. 19, 1999

Related U.S. Application Data

[63] Continuation of application No. PCT/GB97/02556, Sep. 22, 1997.

[30] Foreign Application Priority Data

Sep. 20, 1996 [GB] United Kingdom .................. 9619684

[51] Int. Cl.$^7$ ..................................................... C07F 9/50

[52] U.S. Cl. ............................................. 568/13; 568/17

[58] Field of Search ..................... 568/8, 13, 17

[56] References Cited

U.S. PATENT DOCUMENTS

| 4,178,313 | 12/1979 | Carlock . | |
|---|---|---|---|
| 4,506,030 | 3/1985 | Jones . | |
| 5,399,771 | 3/1995 | Cai ............................................. | 568/17 |
| 5,789,609 | 8/1998 | Tamao ....................................... | 568/18 |

FOREIGN PATENT DOCUMENTS 0 358 129  3/1990  European Pat. Off. .

OTHER PUBLICATIONS

CA: 126:89568 Abs of JP 08311090, Nov. 1996.
Vankelecom, Angewandtre Chenmie. International Edition, 25(12): 1346–1348 (1996).
Sudo et al., J. Chromatogr., 736(1&2) 39–49 (1995).
Bhatt et al., Liq. Cryst., 18(3): 367–80 (1995).
Garcia–Tellado et al., J. Chem. Soc., Chem. Commun., (24), 1761–3 (1991).
Groves et al., J. Org. Chem. 55(11): 3628–34 (1990).
Cuntze et al., Helv. Chim. Acta, 78(2): 367–90 (1995).
Chemical Abstracts, 126(7), 1997, abstract No. 089568, Kai et al.

*Primary Examiner*—Jean F Vollano
*Attorney, Agent, or Firm*—Bacon & Thomas

[57] ABSTRACT

Compounds of Formula (I) wherein R, $R^1$, $R^2$ and $R^9$ are as herein defined, processes for their preparation and transition metal complexes comprising such compounds are disclosed. The complexes may be attached to insoluble supports and are useful as asymmetric catalysts.

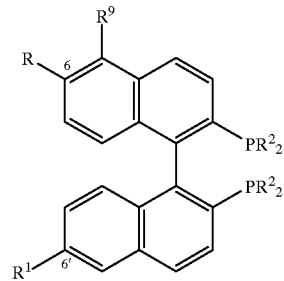

6 Claims, No Drawings

PHOSPHINE LIGANDS

This application is a continuation of international application No. PCT/GB97/02556 filed Sep. 22, 1997 now WO9812202 (of which the entire disclosure of the pending, prior application is hereby incorporated by reference).

This invention relates to new compounds which are suitable for use as ligands for catalysts for use in asymmetric reactions. Such ligands may be attached to an insoluble support in use. This invention also provides a method for the evaluation and use of catalysts comprising such ligands using a combinatorial approach.

Access to enantiomerically pure compounds is essential for the synthesis of natural products, agrochemicals and especially pharmaceuticals. Ideally, asymmetric synthetic techniques are used to produce enantiomerically pure products from prochiral precursors. The most desirable of asymmetric reactions are those employing an asymmetric catalyst. One chiral catalyst molecule can give rise to many chiral product molecules. In addition, catalytic asymmetric synthesis often has significant economical advantages over stoichiometric asymmetric synthesis in the production of enantiomerically pure compounds on an industrial scale. Efforts continue to develop asymmetric reactions with the highest possible stereoselectivity.

A well established class of asymmetric catalysts are transition metal complexes bearing chiral organic ligands. In particular, homogeneous asymmetric catalysis using chiral metal complexes has provided an ideal way to multiply chirality. The appropriate choice of the central metal and the chiral ligand is important for high efficiency of the catalytic process. One important class of catalyst are those based on chiral diphosphines such as 2,2'-bis(diphenylphosphino)-1,1'-binaphthyl (BINAP) (1).

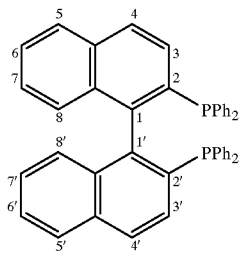

(1)

BINAP has a $C_2$ axis of symmetry and possesses high chemical stability. The free ligand is conformationally flexible enough to accommodate a wide variety of transition metals. Catalysts based on BINAP have shown excellent chiral recognition ability in various asymmetric reactions and BINAP has become one of the more important phosphine ligands for use in producing asymmetric catalysts. (For reviews see Miyashita, A., Takaya, H., Souchi, T., Noyori, R.; *Tetrahedron*, 1245, 40, 1984; European Patent No. 0135392-A2 and European Patent No. 0174057-A2).

In particular the rhodium(I) and ruthenium(II) complexes have been used extensively as chiral catalysts. BINAP coordinated metal complexes have been shown to be efficient catalysts for asymmetric hydrogenation of α-acylaminoacrylic acids and allylic alcohols. They have also been shown to effect an enantioselective 1,3-hydrogen shift of allyl amines to optically active enamines.

Reported examples of highly enantioselective asymmetric reactions utilising BINAP complexes as catalysts include hydrogenation, hydrosilylation, hydroboration of unsaturated compounds, epoxidation of allylic alcohols, vicinal hydroxylation, hydrovinylation, hydroformylation, cyclopropanation, isomerisation of olefins, propylene polymerisation, organometallic addition to aldehydes, allylic alkylation, organic halide-organometallic coupling, aldol type reactions, and Diels-Alder and ene reactions (for reviews see; Noyori, R., *Science* 1990, 248, 1194; Noyori, R., Kitamura, M., in *Modern Synthetic Methods* 1989; Scheffold, R., Ed., Springer-Verlag: Berlin, 1989; p. 115).

BINAP is used to prepare some extremely important industrial catalysts used in asymmetric hydrogenations and isomerisations. Catalysts based on BINAP are currently used in the industrial production of (−)-menthol and carbapenems.

However, in the use of a homogeneous, soluble catalyst such as solution phase BINAP, a problem of practical importance is encountered, namely that the separation of the catalyst from the reaction products becomes difficult, and usually requires special treatment which destroys the catalyst. One way to solve this problem would be to fix the catalyst to an insoluble solid support in a way that retains the advantages observed in solution. In fact homogeneous catalysts have been attached to a variety of supports including cross-linked polymers (for a review see Kohler, N., Dawans, F., *Rev. Inst. Fr. Pet.*, 1972, 27, 105). In this way the catalyst acquires the property of insolubility but may retain the same reactivity exhibited in solution. Once the reaction is completed, the insoluble catalyst may simply be filtered off from the reaction mixture and reused.

BINAP catalysts supported in a thin-film of water or ethylene glycol on the surface of a solid have been reported (Wan, K. T. and Davis, M. E., *Nature*, 370, 449–450 (1994)).

Recently, there have been reports of BINAP based catalysts which are immobilized by trapping them within elastomeric polydimethylsiloxane membranes (I. F. J. Vankelecom et al., *Angew. Chem. Int. Ed. Engl.*, 1996, 35, 1346–1347). The catalysts are not physically attached, such as covalently bonded, in any way to the membrane but are simply trapped within the elastomer network. Indeed, it is specifically stated that it is undesirable to attach the catalyst to the membrane as this may interfere with the chirality of the catalyst and hence with its enantioselectivity in asymmetric reactions. The membranes do allow easier separation of the catalysts from the reaction mixtures but there is still the risk of metal leaching into the reactions and contaminating the products.

It is widely accepted that one of the features attributing to the excellent enantioselectivity of BINAP based catalysts is that BINAP itself possesses a $C_2$ axis of symmetry. This is believed to halve the number of possible diastereomeric intermediates involved in the catalytic process and hence to enhance the enantioselectivity.

There is thus still a need for an asymmetric catalyst which is as effective as those based on BINAP itself in a wide range of reactions, but which may be readily attached to an insoluble support to facilitate purification of the reaction products. There is also a need for improved BINAP derivatives in terms of enantioselectivity and processability (ease of separation and purification of the products and reusability of the catalyst). There is also a need for more rapid exploitation of BINAP catalysts, which may be achieved using a combinatorial evaluation approach.

Surprisingly, it has now been found that derivatives of BINAP itself may be attached to an insoluble support and used as ligands for asymmetric catalysts, without any loss of the catalytic activity or enantioselectivity of the catalyst. This is despite the fact that the attachment of BINAP to an insoluble support may break the $C_2$ symmetry that was previously considered essential for the selectivity of BINAP based catalysts.

According to one feature of the invention, there are therefore provided BINAP derivatives of general formula (I) which may be used as ligands for chiral catalysts:

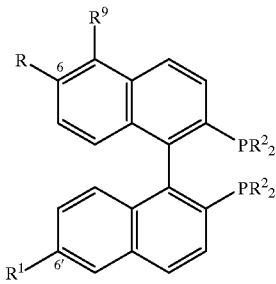

(I)

wherein

R denotes $C_{1-6}$ alkyl, $C_{1-6}$ alkenyl, $C_{1-6}$-alkynyl or phenyl, wherein the $C_{1-6}$ alkyl and phenyl groups may optionally be substituted by one or more substituents which may include F, Cl, Br, $NO_2$, amino, naphthalene, anthracene, biphenyl, $C_{1-6}$ alkyl, $CF_3$, CN, OH, O—$C_{1-6}$ alkyl, $CO_2H$, CHO, NHCO($C_{1-6}$ alkyl), $CO_2$($C_{1-6}$ alkyl), N($C_{1-6}$ alkyl)CO, benzyl, $C_{5-6}$ cyclic ethers or $C_{2-4}$ unsaturated hydrocarbon groups, and wherein the $C_{1-6}$ alkyl group may optionally include one or more intervening heteroatoms or aryl groups in the chain or R denotes CN, $CO_2NHR^3$, $(CH_2)_nOR^3$, $CO_2R^3$, benzyl, heterocyclic groups such as thiophene, furan, pyridine, pyrimidine, quinoline, benzofuran, benzothiophene, pyrrole, imidazole, isoquinoline or indole, wherein the heterocyclic groups may be optionally substituted by one or more ether or $C_{1-6}$ alkyl groups, or Y—X—$R^4$;

$R^1$ denotes R or H;

$R^2$ denotes phenyl, phenyl substituted by one or more $C_{1-7}$ alkyl groups, O—$C_{1-6}$ alkyl groups and/or halogen atoms, or $R^2$ denotes a $C_{3-7}$ cyclic aliphatic hydrocarbon group;

$R^9$ denotes H or together with R forms a 5, 6 or 7 membered hydrocarbon ring, optionally substituted by one or more C=O, OH or amine groups;

Y denotes a straight or branched aliphatic chain, optionally incorporating one or more aromatic hydrocarbon group(s) or ether linkages in the chain, or an aromatic hydrocarbon group;

X denotes $CH_2$, $CO_2$, O, CONH, NH, $CONR^2$, $NR^2$ or a valence bond;

$R^3$ denotes H, $C_1$–$C_{10}$ alkyl, benzyl or phenyl; and $R^4$ denotes H, $C_1$–$C_6$ alkyl, an insoluble support, or a spacer group attached to an insoluble support;

and all enantiomers, mixtures, including racemic mixtures, and diastereomers thereof.

In the above definitions, alkyl represents a straight or branched alkyl group.

The compounds of general formula (I) may be $C_2$ symmetric or non-symmetric. Preferred compounds are those which consist of a single enantiomer (R) or (S) and are enantiomerically pure.

Preferred compounds of general formula (I) are those wherein $R^2$ denotes phenyl;

X denotes CONH or $CO_2$;

Y denotes $(CH_2)_n$ wherein n denotes 2 to 4; and $R^1$ is identical to R.

Further preferred compounds of formula (I) are those wherein $R^4$ denotes an insoluble support or a spacer group attached to an insoluble support.

Especially preferred are compounds of formula (I) wherein $R^2$ denotes phenyl;

$R^4$ denotes an insoluble support or a spacer group attached to an insoluble support;

X denotes CONH or $CO_2$; and

Y denotes $(CH_2)_n$ wherein n denotes 2 to 4.

Especially preferred compounds of formula (I) are shown below. Such compounds may exist in the (R) or (S)-enantiomeric form.

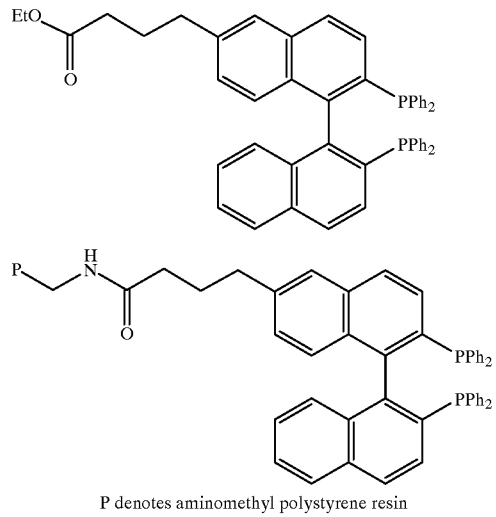

P denotes aminomethyl polystyrene resin

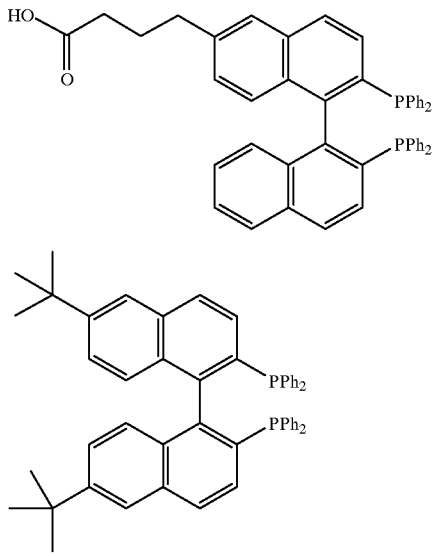

-continued

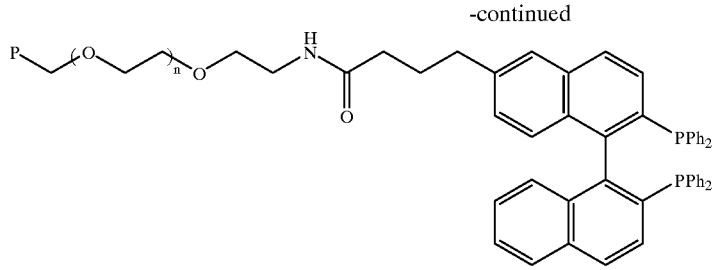

P denotes Tentagel resin
n denotes 50–67

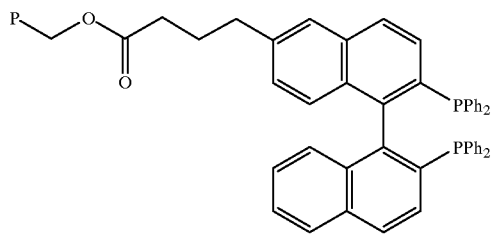

P denotes Wang resin

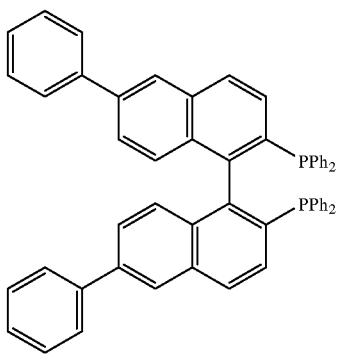

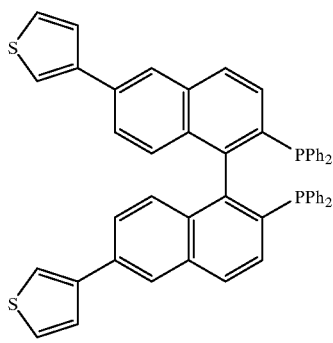

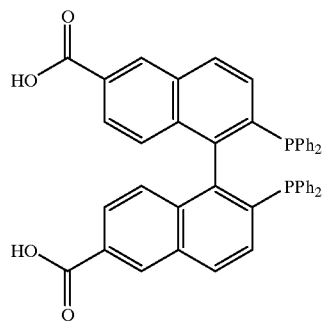

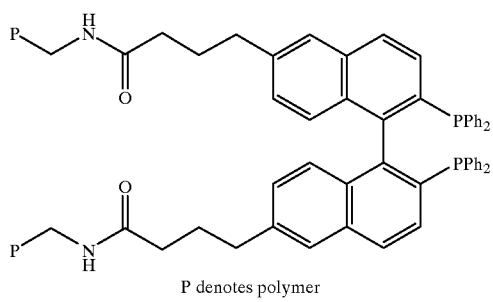

P denotes polymer

Examples of insoluble supports include polystyrenedivinyl benzene co-polymer (Merrifield Resin), polystyrene resin, polyamide, aminomethylated polystyrene resin, Wang resin, aminomethylated Tentagel resin, polyamid-kieselguhr composites, polyhipe, cotton, paper and the like.

Preferred insoluble supports are aminomethyl polystyrene resin, Wang resin and Tentagel resin.

The attachment of the X group to the insoluble support may be direct or via a spacer group. Examples of possible spacer groups include alkylene chains and alkylene chains interrupted by ether, amino, ester and/or amide linkages.

The ligands of general formula (I) may be complexed to any transition metal for which BINAP itself is a ligand. Particularly preferred metals for the preparation of asymmetric catalysts are rhodium, ruthenium, and palladium, especially ruthenium.

In a further feature of the invention there are provided complexes comprising a compound of formula (I) complexed to a transition metal.

Such complexes are of use as potential asymmetric catalysts. Such catalysts may be used enantio-selectively in solution or when attached to an insoluble support.

In such complexes, the vacant coordination sites on the metal may be occupied by any ligands which complex to the metal in conventional BINAP-based catalysts, or any other ligands which do not affect the catalytic activity of the complex. Such ligands include, but are not limited to, Cl, Br, I, F, allyl, $OCOCH_3$, H, $PCl_6$, $PF_6$, $ClO_4$, $BF_4$, tetraphenylborate, benzene, p-cymene, 1,5-cyclooctadiene, acetylacetonate anion (acac) or tertiary amines such as $NEt_3$.

Possible transition metals include rhodium, ruthenium, palladium, iridium, nickel, cobalt and molybdenum. Particularly preferred for use as asymmetric catalysts are ruthenium, rhodium or palladium complexes.

Preferred for use as asymmetric catalysts are complexes of empirical formula $LRuBr_2$ wherein L denotes a ligand of general formula (I).

Preferred ligands L are compounds of formula (II)

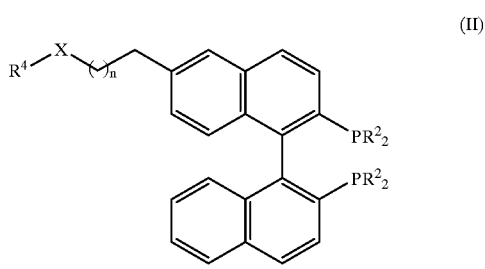

(II)

wherein

X denotes $CO_2$, O, NH, CONH, $CH_2$ or a valence bond;

n denotes 0–9; and $R^2$ and $R^4$ are as hereinbefore defined.

The BINAP derivatives of formula (I) may be synthesised in solution and then, if desired, they may be attached to an insoluble solid support using conventional methodology. Attachment to the support may be, for example, by the formation of an amide, ether, amino, ester or carbon-carbon linkage. Scheme 1 illustrates the synthesis of a support-bound compound of formula (I).

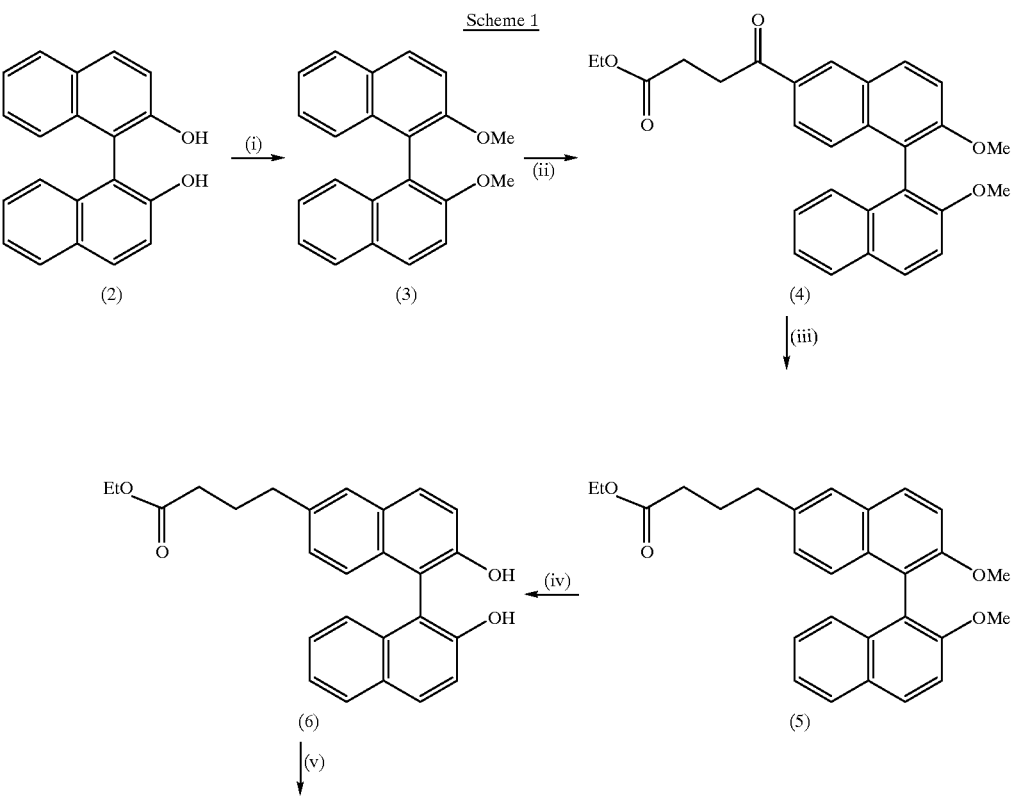

Scheme 1

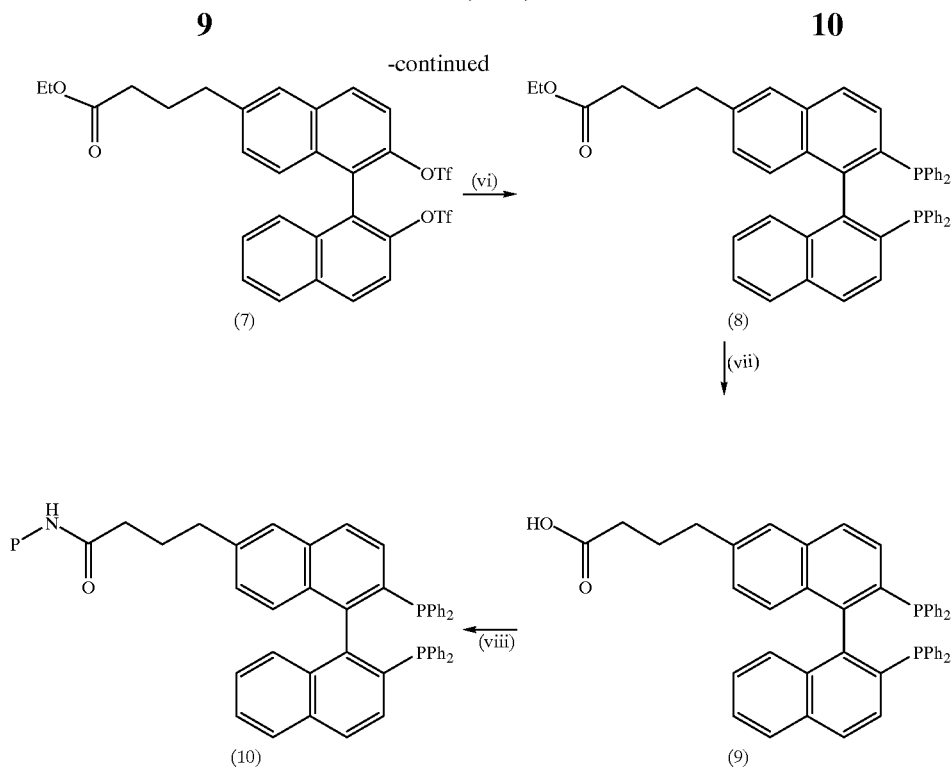

(i) MeI, K₂CO₃, acetone, reflux; (ii) EtO₂C(CH₂)₂COCl, AlCl₃, CH₂Cl₂; (iii) H₂, Pd/C, CH₃SO₃H, AcOH, EtOAc, EtOH; (iv) BBr₃, CH₂Cl₂; (v) Tf₂O, 2,6-lutidine, DMAP, CH₂Cl₂; (vi) HPPh₂, NiCl₂dppe, DABCO, DMF, 100° C. then EtOAc, NaCN then PhCH₃, SiHCl₃; (vii) LiOH, THF, reflux; (viii) DIC, HOBt, DIPEA, CH₂Cl₂, DMF, aminomethylated polystyrene resin (P).

The starting material is enantiomerically pure 1,1'-bi-2-naphthol (2) (BINOL), which is commercially available in either the R-form or the S-form. The synthetic scheme does not affect the chiral integrity of the products. Use of one enantiomer of BINOL as the starting material leads to one enantiomeric product BINAP derivative. Use of the other enantiomer of BINOL as starting material will give the opposite enantiomer of the product.

The alcohol functionalities in BINOL (2) are protected as ethers and a selective Friedel-Crafts acylation is carried out to derivatise one of the naphthyl groups in the 6-position. It was then found necessary to reduce the benzylic carbonyl group in compound (4) to the corresponding methylene group in order to deprotect the methyl ethers. Deprotection of the alcohol groups in compound (4) is followed by a ditriflation. This step is well known in the art for the synthesis of BINAP itself. The phosphine groups are then introduced by displacement of the triflate groups to give compound (8). The side chain may then be further modified and subsequently attached to an insoluble support if required.

Other compounds of the invention may be prepared using analogous procedures to those illustrated in Scheme 1.

As a further feature of the invention there are provided intermediates of formula (III), which may be used in the synthesis of compounds of formula (I).

(III)

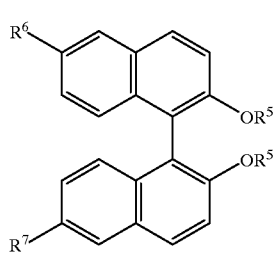

wherein
R⁵ denotes any alkyl group which directs substitution to the 6 position, in particular R⁵ denotes $C_{1-7}$ alkyl, especially $(CH_2)_{0-6}CH_3$, or a $C_{3-7}$ cyclic aliphatic group; and
R⁶ denotes Cl, a straight or branched acyl or non-acyl aliphatic chain, optionally terminating in an acid functionality and optionally incorporating one or more aromatic hydrocarbon, ether, ester or amide groups within the chain or terminating the chain; or R⁶ denotes a phenyl group, optionally substituted by one or more F, Cl, Br, $NO_2$, amino, naphthalene, anthracene, biphenyl, $C_{1-6}$ alkyl, $CF_3$, CN, OH, O—$C_{1-6}$ alkyl, $CO_2H$, CHO, NHCO($C_{1-6}$ alkyl), $CO_2(C_{1-6}$ alkyl), N($C_{1-6}$ alkyl)CO, benzyl, $C_{5-6}$ cyclic ethers or $C_{2-4}$ unsaturated hydrocarbon groups, or R⁶ denotes a heterocyclic group such as thiophene, furan, pyridine, pyrimidine, quinoline, benzofuran, benzothiophene, pyrrole, imidazole, isoquinoline or indole, wherein the heterocyclic groups may be optionally substituted by one or more ether or $C_{1-6}$ alkyl groups; and
R⁷ denotes R³ or H;
with the provisos that
a) when R⁵ denotes methyl and R⁷ denotes H, then R⁶ does not denote —CO(CH₂)₃COOCH₃, —CO(CH₂)₃COOH or —(CH₂)₄COOH; and b) when $R^5$ denotes methyl and $R^7$ denotes $R^6$, then $R^6$ does not denote $C_8H_{18}$.

Substitution in the 6-position gives a handle via which the BINAP derivatives of the invention may be attached to an insoluble solid support. Derivatisation in the 6-position, or at both the 6 and 6' positions, may be achieved via, for example, Friedel-Crafts acylation, Friedel-Crafts alkylation, Friedel-Crafts arylation or Suzuki, Heck or Stille coupling reactions on suitable precursors.

Compounds of formula (III) may be synthesised from suitably protected BINOL (2) derivatives of formula (IV). It has now been found that Friedel-Crafts reactions of such compounds proceed highly selectively, depending on the reaction conditions, at either the 6 position or at both the 6 and 6' positions of the naphthyl rings in the compounds of formula (IV).

As a further feature of the invention there is therefore provided a process for the synthesis of compounds of general formula (III) according to Scheme 2.

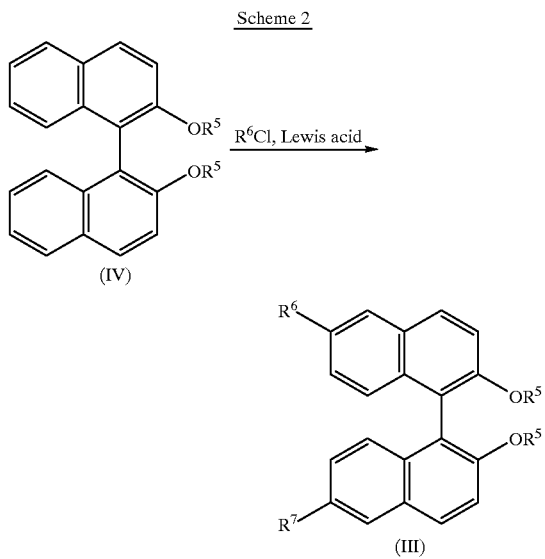

Scheme 2 wherein
$R^5$, $R^6$ and $R^7$ are as hereinbefore defined, with the proviso that $R^6$ does not denote Cl.

Suitable Lewis acids include $AlCl_3$, $TiCl_4$, $SnCl_4$, $FeCl_3$, $I_2$, $ZnCl_2$, $BeCl_2$, $CdCl_2$, $BF_3$, $BCl_3$, $BBr_3$, $GaCl_3$, $GaBr_3$, $TiBr_4$, $ZrCl_4$, $SnBr_4$, $SbCl_5$, $SbCl_3$ or $BiCl_3$. A particularly preferred Lewis acid is $AlCl_3$.

Use of a large molar excess of the reagent $R^6Cl$ tends to favour formation of the disubstituted products ($R^6=R^7$ in formula (III)). Use of just over one mole equivalent of the reagent $R^6Cl$ tends to favour formation of monosubstituted products ($R^7=H$ in formula (III)).

Alternatively, the 6,6'-disubstituted compounds of the invention may be prepared via elaboration of simple, known 6,6'-disubstituted BINOL derivatives. (R)-6,6'-dibromo-1,1'-bi-2-naphtol may be prepared according to the literature procedure in *J. Am. Chem. Soc.*, 1979, 101, 3035–3042, while (R)-6,6'-dibromo-2,2'-dimethoxy-1,1'-binaphtyl and (R)-6,6'-dicyano-1,1'-bi-2-naphtol may be prepared according to the literature procedures in *J. Org. Chem.*, 1995, 60, 7388.

For example, the bromo groups in the known compound (R)-6,6'-dibromo-1,1'-bi-2-naphtol may be replaced by aromatic or heterocyclic rings via Suzuki coupling reactions with suitable boronic acid or boronic ester derivatives. For example, treatment of (R)-6,6'-dibromo-1,1'-bi-2-naphtol with thiophene-3-boronic acid may yield (R)-6,6'-di-(3-thienyl)-1,1'-bi-2-naphtol, whilst treatment with phenyl boronic acid may yield the corresponding 6,6'-diphenyl derivative.

The cyano groups in suitably protected derivatives of the known (R)-6,6'-dicyano-1,1'-bi-2-naphtol may be hydrolysed to yield the corresponding 6,6'-diacid derivatives. The acid groups may then be further elaborated as required using conventional synthetic techniques.

The 6,6'-disubstituted BINOL derivatives may then be converted into the corresponding BINAP compounds of the invention by analogous processes to those mentioned above and illustrated in Scheme 1.

As a further feature of the invention there is provided a process for the preparation of compounds of formula (I) which comprises converting the $OR^8$ groups in a compound of formula (III) into leaving groups which may be displaced by $HP_2^2$, reacting the resultant product with $HPR_2^2$, wherein $R^2$ is as hereinbefore defined and, if necessary, performing synthetic chemistry to convert the $R^6$ and $R^7$ groups into R and $R^1$ groups respectively.

The introduction of the phosphine groups into the compounds of the invention may be achieved by displacement of a leaving group in a compound of formula (V) by diphenylphosphine or a suitably substituted is derivative of diphenylphosphine. As a further feature of the invention there is therefore provided a process for the synthesis of compounds of formula (I) from compounds of formula (V), as shown in Scheme 3.

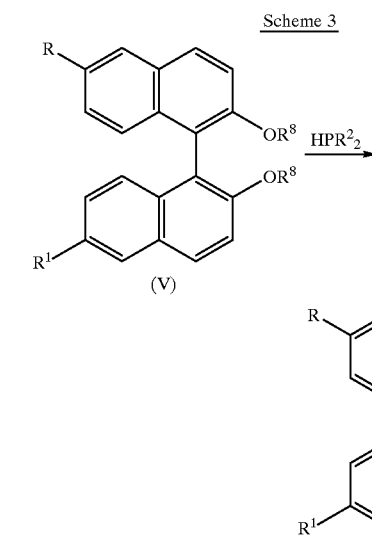

Scheme 3 wherein $OR^8$ denotes a leaving group which may be displaced by $HR_2^2P$, preferably $OSO_2CF_3$ (OTf); and R, $R^1$ and $R^2$ are as hereinbefore defined.

As a further feature of the invention there are provided compounds of formula (V)

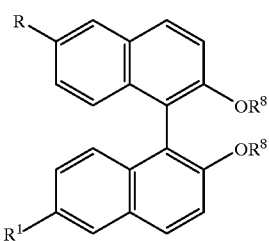

(V)

wherein
  $OR^8$ denotes a leaving group which may be displaced by $HPR_2^2$, preferably $OSO_2CF_3$ (OTf); and
  R and $R^1$ are as hereinbefore defined.

An alternative method for the introduction of the phosphine groups into the compounds of the invention is via the displacement of bromo groups with suitably substituted derivatives of chlorodiphenylphosphine oxide ($R_2^2POCl$, wherein $R^2$ is as defined above), in an analogous process to that known for the preparation of BINAP itself (Noyori et al., *J. Org. Chem.*, 1986, 51, 629–635). The resulting phosphine oxide derivatives may then be reduced to the phosphine derivatives by treatment with a reducing agent such as trichlorosilane in the presence of triethylamine.

The BINAP derivatives of general formula (I) may be complexed to transition metals using methods well known in the art for the synthesis of BINAP based catalysts.

The complexes of the invention may be produced in situ, used without isolation and may be reused after appropriate work-up or regeneration.

Asymmetric catalysts comprising compounds of formula (I) are useful in the same type of reactions as are conventional BINAP catalysts. In particular, they are of use in the much used asymmetric reductions but their use is not limited to these reactions. As a further feature of the invention there is therefore provided the use of complexes comprising a compound of formula (I) and a transition metal as catalyst in asymmetric reduction reactions, especially in hydrogenations.

Surprisingly, it has been found that the introduction of substituents at the 6-position of BINAP does not affect its ability to act as a chiral ligand in asymmetric catalysts. In particular, it has been found that non-$C_2$ symmetric BINAP catalysts induce the same high enantioselectivity in asymmetric reactions as does the $C_2$ symmetric BINAP molecule itself. Comparison of reactions using catalysts based on BINAP itself and on non-$C_2$ symmetric BINAP derivatives show very similar yields and enantiomeric excesses for both types of catalysts.

The attachment of the BINAP derivatives of the invention to an insoluble support causes, in the majority of cases, little or no reduction in the enantioselectivity of the catalysts compared to the corresponding unsubstituted BINAP catalysts in solution. The attachment may be via only the 6 position of the BINAP derivative of formula (I) or via positions on both naphthyl groups. Such support-bound BINAP derivatives may or may not possess a $C_2$ symmetry axis. The optimal loading of the insoluble support is 0.1–1.0 millimole equivalents per gram, preferably 0.2–0.4 millimole equivalents per gram. The loading of the support may be assessed by weight gain.

The use of such pseudo-heterogeneous catalysts leads to much simpler work-up and purification procedures than does the use of catalysts comprising BINAP itself. The catalyst attached to the solid support is simply filtered off and the resulting filtrate is concentrated to give the desired chiral product with no traces of catalyst or metal complexes contaminating it. Additionally, if the catalyst is filtered off under an inert atmosphere it may be reused without any or only slight reduction in enantioselectivity. The catalyst may be regenerated on the polymer or the polymer bound catalyst may simply be dried and re-used. This is in contrast to homogeneous BINAP catalysts, which may be difficult to remove from the reaction products. In practice, removal of conventional catalysts may entail poisoning the catalyst, therefore removing any hope of re-using it. The potential to re-use the support-bound catalysts of the invention makes them economically attractive compared to conventional BINAP catalysts.

Catalysts comprising the ligands of the invention can be rapidly evaluated using combinatorial chemistry techniques. Combinatorial chemistry (for reviews see Thompson, L. A., Ellman, J. A., *Chem. Rev.* 1996, 96, 555; Terrett, N. K., Gardner, M., Gordon, D. W., Kobylecki, R. J., Steele, J., *Tetrahedron* 1995, 51, 8135; Lowe, G., *Chem. Soc. Rev.*, 1995 309) is a specialist technique whereby large numbers of molecules may be synthesised with minimal synthetic effort. A key feature of combinatorial chemistry is that compound synthesis is designed such that a range of analogues can be produced using similar reaction conditions, either in the same vessel or individually in parallel using semi-automated synthesis. This has for the most part been used to synthesise large libraries of structurally distinct molecules, such as peptides, for biological evaluation within the pharmaceutical or agrochemical industries.

Using specialist apparatus, it is possible to screen a variety of ligands against various substrates under specific reaction conditions. Such apparatus is designed to allow automation of the reactions. For example, for screening catalysts for use in hydrogenation reactions, a high pressure reactor is used which can accommodate a multi vessel reaction block. The use of a solid teflon reaction block in conjunction with a stirrer hot plate, for example an IKAL-abortechnik RCT basic hot plate stirrer, is preferred. This allows the provision of sufficient heating and mixing of the reaction mixtures, a sufficient supply of hydrogen gas and a suitable amount of sample in each reaction vessel.

The method may be exemplified with reference to the is insoluble solid supported bound catalysts of the invention. These support bound catalysts have the advantage that after completion of the reaction, they may simply be filtered off from the products. If the catalyst is filtered off under an inert atmosphere it may be reused or regenerated. The reaction mixtures may be filtered directly into another identical reaction block from which the reaction solvents may be evaporated. The contents of each individual reaction vessel may then be analysed in terms of optical purity, reaction purity, conversion and yield. This allows rapid identification of optimum reaction conditions for a specific reaction and/or substrate. It is anticipated that under optimum reaction conditions it will be possible to achieve optical purities of up to 99% or higher.

This method of screening/evaluating ligands and catalysts may also be used for the solution phase catalysts of the invention, and indeed for the evaluation of other classes of chiral catalysts in solution or when bound to insoluble supports.

The following Examples are non-limiting illustrations of the invention.

EXAMPLES

Example 1
Preparation of (R)-2,2'-dimethoxy-1,1'-binaphthyl (3)

To a well stirred solution of (R)-BINOL (2) (18.85 g, 0.0659 mol) in anhydrous acetone (600 ml) was added anhydrous $K_2CO_3$ (27.30 g, 0.198 mol) and methyl iodide (28.08 g 0.198 mol). The mixture was heated at reflux under a calcium chloride guard tube for 18 hours. After cooling, the volatiles were removed in vacuo and the residual solids dissolved in $CH_2Cl_2$ (600 ml) and $H_2O$ (500 ml). The layers were separated and the aqueous phase extracted with $CH_2Cl_2$ (3×200 ml). The combined organic layers were dried over anhydrous $Na_2CO_3$ and the solvent removed in vacuo to leave a pale yellow solid. Purification by washing with MeOH (3×50 ml) and drying under reduced pressure yielded (R)-2,2'-dimethoxy-1,1'-binaphthyl (3) as a white solid (18.8 g, 90%).

1H NMR (300 MHz, $CDCl_3$): $\delta_H$ 3.80 (6H, s), 7.13 (2H, d, J=8 Hz), 7.23 (2H, dd, J=9, 12 Hz), 7.33 (2H, t, J=9 Hz), 7.48 (2H, d, J=12 Hz), 7.87 (2H, d, J=8 Hz), 8.00 (2H, d, J=9 Hz).

Alternative Preparation of (3)

A mixture of (R)-BINOL (2) (8787 g, 1 mole equivalent), methyl iodide (5 mole eq.) and potassium carbonate (4 mole eq.) in acetone (7.5 vol.) was heated at reflux for 36 hours. The reaction mixture was allowed to cool to room temperature, and the solids removed by filtration. The residual solids were then washed with water (3×5 vol.), to remove inorganic material, and ethyl acetate (1×4 vol.), and dried in a vacuum oven at 40° C. overnight. The desired product was obtained as a white solid in 94% yield (9046 g).

(1 Volume of solvent corresponds to 1 liter per kg of substrate).

Example 2
Preparation of (R)-acylated dimethoxyBINOL (4)

To a cooled (0° C.) solution of (R)-2,2'-dimethoxy-1,1'-binaphthyl (3) (8.46 g, 0.027 mol) in $CH_2Cl_2$ (200 ml) under argon was added solid $AlCl_3$ (3.94 g, 0.030 mol) The red solution was stirred for 10 minutes and to this was added dropwise ethyl succinyl chloride (4.88 g, 0.030 mol). The resulting brown solution was warmed to room temperature, stirred for 18 hours and then poured carefully onto $H_2O$ (200 ml). The layers were separated and the aqueous phase extracted with $CH_2Cl_2$ (2×100 ml). The combined organic fractions were dried over anhydrous $Na_2SO_4$ and the solvents removed in vacuo. Purification was affected by flash column chromatography (silica gel, EtOAc-hexane, 30%) to yield the title product (R)-(4) as a white solid (7.15 g, 60%).

1H NMR (300 MHz, $CDCl_3$): $\delta_H$ 1.28 (3H, t, J=7 Hz), 2.80 (2H, t, J=8 Hz), 3.41 (2H, t, J=8 Hz), 3.75 (3H, s), 3.79 (3H, s), 4.18 (2H, q, J=7 Hz), 7.10 (1H, d, J=9 Hz), 7.20 (1H, d, J=9 Hz), 7.24 (1H, t, J=9 Hz), 7.33 (1H, t, J=9 Hz), 7.48 (1H, d, J=9 Hz), 7.52 (1H, d, J=9 Hz), 7.80 (1H, d, J=9 Hz), 7.89 (1H, d, J=9 Hz), 8.00 (1H, d, J=9 Hz), 8.12 (1H, d, J=9 Hz), 8.57 (1H, s).

Example 3
Preparation of (R)-hydrogenated dimethoxyBINOL (5)

A flask containing (R)-(4) (5.44 g, 0.0123 mol), 10% Pd on carbon (0.75 g), methanesulphonic acid (1.42 g, 0.0148 mol), acetic acid (2.5 ml), EtOAc (85 ml) and EtOH (85 ml) was thoroughly purged with argon and then hydrogen. The reaction mixture was stirred under an atmosphere hydrogen for 18 hours, filtered through celite and the solvents removed in vacuo. The residue was dissolved in EtOAc (100 ml) and treated with saturated aqueous $NaHCO_3$ (100 ml). The phases were separated and the aqueous layer extracted with EtOAc (3×30 ml). The combined organic extracts were dried ($Na_2CO_3$) and the volatiles removed in vacuo. Purification by flash column chromatography (silica gel, EtOAc-hexane, 15%) yielded the title product (R)-(5) as a clear oil which solidified upon standing (4.20 g, 80%).

1H NMR (300 MHz, $CDCl_3$): $\delta_H$ 1.22 (3H, t, J=7 Hz), 1.95–2.08 (2H, m), 2.31 (2H, t, J=8 Hz), 2.72 (2H, t, J=8 Hz), 3.74 (3H, s), 3.78 (3H, s), 4.12 (2H, q, J=7 Hz), 7.01–7.08 (2H, m), 7.09 (1H, d, J=9 Hz), 7.17–7.27 (1H, m), 7.29 (1H, t, J=9 Hz), 7.40–7.47 (2H, m), 7.61 (1H, s), 7.84 (1H, d, J=9 Hz), 7.92 (1H, d, J=9 Hz), 7.98 (1H, d, J=9 Hz).

Example 4
Preparation of (R)-demethylated material (6)

To a cooled (−78° C.) solution of (R)-(5) (0.99 g, 2.31 mmol) in anhydrous $CH_2Cl_2$ (15 ml) was added dropwise a 1.0 M $CH_2Cl_2$ solution of $BBr_3$ (5.1 ml, 5.10 mmol). The mixture was warmed slowly to room temperature, stirred for 1.5 hours and poured carefully onto saturated aqueous $NaHCO_3$ (50 ml). The layers were separated and the organic phase extracted with $CH_2Cl_2$ (3×20 ml). The combined organic layers were dried over anhydrous $Na_2CO_3$ and the solvent removed in vacuo. Flash column chromatography (silica gel, EtOAc-hexane, 20%) provided the title product (R)-(6) as a white solid (0.69 g, 75%).

1H NMR (300 MHz, $CDCl_3$) $\delta_H$ 1.23 (3H, t, J=7 Hz), 1.98–2.03 (2H, m), 2.32 (2H, t, J=8 Hz), 2.75 (2H, t, J=8 Hz), 4.11 (2H, q, J=7 Hz), 5.02 (1H, s), 5.10 (1H, s), 7.08 (1H, d, J=9 Hz), 7.16 (2H, d, J=9 Hz), 7.27–7.42 (4H, m), 7.58 (1H, s), 7.85–7.90 (2H, m), 7.97 (1H, d, J=9 Hz).

Example 5
Preparation of (R)-ditriflate (7)

To a cooled (0° C.) mixture of (R)-(6) (0.67 g, 1.68 mmol), 2,6-lutidine (0.45 g, 4.19 mmol) and 4-dimethylaminopyridine (0.020 g, 0.169 mmol) was added dropwise trifluoromethanesulphonic anhydride (1.04 g, 3.69 mmol). The resulting orange solution was warmed to room temperature, stirred for 20 hours and then poured onto saturated aqueous $NaHCO_3$ (20 ml). The layers were separated and the aqueous phase extracted with $CH_2Cl_2$ (3×15 ml). The combined organic layers were washed with 0.5 M aqueous HCl (20 ml) and $H_2O$ (20 ml) then dried over anhydrous $Na_2CO_3$. Removal of the solvent in vacuo and purification by flash column chromatography (silica gel, EtOAc-hexane, 15%) gave the title product (R)-(7) as a colourless oil (0.92 g, 83%).

1H NMR (300 MHz, $CDCl_3$): $\delta_H$ 1.26 (3H, t, J=7 Hz), 2.02–2.10 (2H, m), 2.37 (2H, t, J=8 Hz), 2.82 (2H, t, J=8 Hz), 4.13 (2H, q, J=7 Hz), 7.18 (1H, d, J=9 Hz), 7.24–7.29 (2H, m), 7.41 (1H, t, J=9 Hz), 7.58–7.66 (3H, m), 7.79 (1H, s), 8.01 (1H, d, J=9 Hz), 8.07 (1H, d, J=9 Hz), 8.14 (1H, d, J=9 Hz).

Example 6
Preparation of (R)-diphosphine (8)

A solution of $NiCl_2$dppe (2.12 g, 4.01 mmol) in anhydrous DMF (10 ml) was degassed thoroughly using 7 pump/argon cycles. $HPPh_2$ (1.24 g, 6.68 mmol) was added and the red mixture aged at 100° C. for 1 hr. In a separate flask degassed (R)-(7) (2.22 g, 3.34 mmol) and 1,4-diazabicyclo[2.2.2]octane (1.50 g, 0.0134 mol) in DMF (10 ml) and added to the nickel solution via canula. The resulting deep green solution was heated at 100° C., a further portion of $HPPh_2$ (1.24 g, 6.68 mmol) added after 4 hours and continued heating for a further 16 hours. After cooling to room temperature the mixture was diluted with EtOAc (50 ml), poured onto 50 ml aqueous NaCN (1.64 g, 0.0334 mmol) and stirred vigorously for 1 hr. The layers were separated and the organic phase washed with $H_2O$ (3×20 ml), dried over anhydrous $Na_2SO_4$ and the solvents removed in vacuo. The resulting brown solid was then dissolved in anhydrous toluene (50 ml), treated with trichlorosilane (13.42 g, 0.099 mol) and heated at reflux for 18 hours. The mixture was quenched by pouring carefully onto 2.0 M aqueous NaOH (100 ml) and stirring vigorously for 30 mins. The layers were separated and the aqueous phase extracted with $CH_2Cl_2$ (3×20 ml). The combined organic layers were dried over anhydrous $Na_2CO_3$ and the volatiles removed in vacuo. Purification was affected by flash column chromatography (silica gel, EtOAc-hexane, 10%) to give the title product (R)-(8) as a white solid (1.64 g, 66%).

1H NMR (300 MHz, $CDCl_3$): $\delta_H$ 1.30 (3H, t, J=7 Hz), 1.94–2.03 (2H, m), 2.31 (2H, t, J=8 Hz), 2.72 (2H, t, J=8 Hz), 4.16 (2H, q, J=7 Hz), 6.71 (2H, s), 6.89 (1H, d, J=9 Hz), 6.95 (1H, t, J=9 Hz), 7.06–7.25 (10H, m), 7.37 (1H, t, J=9 Hz), 7.48 (2H, d, J=9 Hz), 7.62 (1H, s), 7.83–7.88 (2H, m), 7.92 (1H, d, J=9 Hz).

Example 7
Preparation of (R)-acid (9)

To a solution of (R)-(8) (1.48 g, 2.01 mmol) in THF (15 ml) was added 15 ml aqueous LiOH (4.0 g, 0.10 mol) and the mixture heated at reflux for 20 hours. After cooling to room temperature the solution was acidified to pH 3 with 2.0 M aqueous HCl and extracted with EtOAc (3×20 ml). The combined organic extracts were dried over anhydrous $Na_2CO_3$ and the solvent removed in vacuo. Recrystallisation from methanol afforded the title compound (R)-(9) as a white solid (1.43 g, 99%).

Example 8
Aninomethyl polystyrene supported BINAP (10)

Aminomethyl polystyrene resin (1.0 g, 0.21 mmol) was swollen with $CH_2Cl_2$ (5 ml). (R)-9 (0.223 g, 0.315 mmol) was added as a solution in DMF (5 ml) followed by hydroxybenzotriazole (0.064 g, 0.42 mmol), is diisopropylethylamine (0.030 g, 0.21 mmol) and diisopropylcarbodiimide (0.056 g, 0.44 mmol). The resulting mixture was stirred slowly for 24 hr. The resin was collected by filtration and washed sequentially with DMF (2×5 ml), $CH_2Cl_2$ (2×5 ml), MeOH (2×5 ml) and $Et_2O$ (2×5 ml). Drying under vacuum afforded a white coloured resin (R)-10 (1.148 g, quantitative loading) to be used in asymmetric hydrogenation reactions.

Example 9
Asymmetric Hydrogenations, Typical Catalyst Preparation

To a mixture of (R)-diphosphine-resin (10) (30 mg, 0.0063 mmol) and bis-(2-methylallyl)cycloocta-1,5-dieneruthenium (II) complex (2 mg, 0.0063 mmol) in anhydrous degassed acetone (0.5 ml) was added 0.29 M methanolic HBr (0.043 ml, 0.0125 mmol). The amber mixture was stirred at room temperature for 1 hr and the solvent removed thoroughly in vacuo to leave the coloured active resin which was used immediately as a hydrogenation catalyst.

Example 10
Typical Hydrogenation Procedure

A solution of methyl propionylacetate (41 mg, 0.314 mmol) in degassed THF (0.3 ml) and MeOH (0.3 ml) was added to catalyst in a glass vial and placed into a stainless steel pressure vessel. The system was thoroughly purged with hydrogen by three cycles of pressurising and stirred magnetically with heating at 50° C. under 10 atmospheres of hydrogen pressure for 18 hr. After cooling the reaction mixture was filtered and the resin washed with THF (3×1 ml). Removal of solvent in vacuo furnished the β-hydroxy ester which was analysed without purification. Enantiomeric excess=96.9%.

1H NMR (300 MHz, $CDCl_3$): $\delta_H$ 0.95 (3H, t, J=6 Hz), 1.43–1.60 (2H, m), 2.42 (1H, dd, J=9, 12 Hz), 2.53 (1H, dd, 4, 12 Hz), 2.96 (1H, s), 3.72 (3H, s), 3.90–4.00 (1H, m).

Example 11
(R)-6,6'-Di-t-butyl-2,2'-dimethoxy-1,1'-binaphthyl

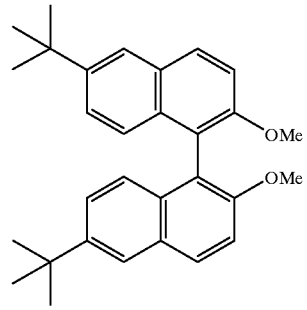

t-Butyl chloride (3.0 g, 31.8 mM) was added to a stirred solution of (R)-2,2'-dimethoxy-1,1'-binaphthyl (3) (1.0 g, 3.18 mM) in dichloromethane (30 ml) at −78° C. under an atmosphere of argon. To the mixture was added aluminium chloride (4.24 g, 31.8 mM) and the mixture stirred for a further 6 hours at −78° C. The reaction mixture was allowed to warm to room temperature and quenched by the dropwise addition of water (50 ml). Dichloromethane (2×30 ml) was added and the organic layers were separated, dried over magnesium sulphate, filtered and the solvent removed in vacuo. Purification by column chromatography eluting with 30% ethyl acetate:hexane gave the title compound (1.1 g, 81% ) as a white solid.

Example 12
(R)-6,6'-Di-t-butyl-1,1'-bi-2-naphthol

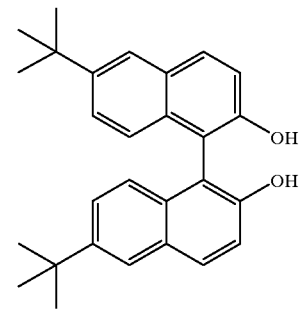

To a pre-cooled (−78° C.) stirred solution of (R)-6,6'-di-t-butyl-2,2'-dimethoxy-1,1'-binaphthyl (1.08 g, 2.92 mM), prepared according to Example 11, in dichloromethane (10 ml) under an atmosphere of argon was added dropwise boron tribromide (0.6 ml, 5.82 mM). The resulting black solution was allowed to warm to room temperature and stirred for 2 hours. The reaction mixture was quenched by the dropwise addition of water (10 ml), and the resulting phases separated. The aqueous phase was washed with dichloromethane (2×20 ml) and the combined organic extracts dried over sodium sulphate and concentrated in vacuo. Purification by column chromatography eluting with 20% ethyl acetate: hexane gave the title compound as a colourless oil (0.91 g, 91%).

Example 13
(R)-6,6'-di-t-butyl-2,2'-ditrifluoromethansulphonate-1,1'-binaphthyl

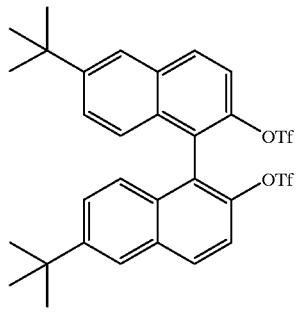

Trifluoromethanesulphonic anhydride (0.6 ml, 3.6 mM) was added to a stirred solution of (R)-6,6'-di-t-butyl-1,1'-bi-2-naphthol (1.19 g, 3.5 mM), prepared according to Example 12, 4-dimethylaminopyridine (6 mg) and 2,6-lutidine (1.0 ml) in dichloromethane (10 ml) at 0° C. under an atmosphere of argon. The reaction mixture was allowed to warm to room temperature and stirred for a further 16 hours. Saturated sodium bicarbonate solution (10 ml) was added to the reaction mixture to quench and the organic layer separated. The aqueous phase was washed successively with dichloromethane (2×15 ml). The combined organic extracts were dried over sodium sulphate and the solvent removed in vacuo to give an oil. Purification by column chromatography eluting with 1% ethyl acetate:hexane gave the title compound as a colourless oil (1.63 g, 85%).

Example 14
(R)-di-t-butyl-2,2'-bis(diphenylphosphino)-1,1'-naphthyl

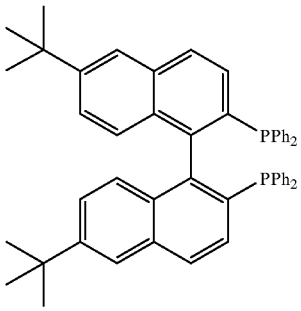

A solution of NiCl$_2$dppe (1.13 g, 2.14 mM) in anhydrous dimethylformamide (10 ml) was degassed thoroughly using 7 pump/argon cycles. Diphenylphosphine (0.62 ml, 1.9 mM) was added and the red mixture aged at 100° C. for 1 hour. In a separate flask were degassed (R)-6,6'-di-t-butyl-2,2'-ditrifluoromethanesulphonate-1,1'-binaphthyl (1.0 g, 1.65 mM), prepared according to Example 13, and 1,4-diazabicyclo[2.2.2]octane (0.81 g, 7.2 mM) in dimethylformamide (10 ml) and added to the nickel solution via canula. The resulting deep green solution was heated at 100° C., a further portion of diphenylphosphine (0.62 ml, 1.9 mM) added after 4 hours and continued heating for a further 16 hours. After cooling to room temperature the mixture was diluted with ethyl acetate (30 ml), poured onto 50 ml aqueous sodium cyanide (0.86 g, 17.9 mM) and stirred vigorously for 1 hour. The layers were separated and the organic phase washed with water (3×20 ml), dried over anhydrous sodium sulphate and the solvents removed in vacuo. The resulting brown solid was then dissolved in anhydrous toluene (30 ml), treated with trichlorosilane (0.97 g, 0.73 mM) and heated at reflux for 18 hours. The mixture was quenched by pouring carefully onto 2.0 M aqueous sodium hydroxide (30 ml) and stirring vigorously for 30 minutes. The layers were separated and the aqueous phase extracted with Dichloromethane (3×25 ml). The combined organic layers were dried over anhydrous sodium carbonate and the solvent removed in vacuo. Purification was effected by flash column chromatography (silica gel, ethyl acetate-hexane, 10%) to give the title compound as a white solid (0.75 g, 62%).

Example 15
(R)-6,6'-Dibromo-2,2'-dibenzoxy-1,1'-binaphthyl

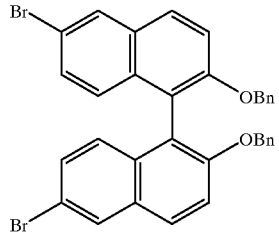

(R)-6,6'-Dibromo-1,1'-bi-2-naphthol (0.50 g, 1.13 mM), prepared according to the literature procedure in *J. Am. Chem. Soc.* 1979, 101, 3035–3042, benzyl bromide (0.40 ml, 3.38 mM) and potassium carbonate (0.78 g, 5.65 mM) were stirred in refluxing acetone (10 ml) under an atmosphere of argon for 18 hours. After cooling to room temperature, the reaction mixture was poured into dichloromethane (25 ml) and water (25 ml). The layers were separated and the aqueous layer extracted with dichloromethane (2×25 ml). The combined organic layers were dried over sodium sulphate, filtered and the solvent removed in vacuo. The residue was purified by trituration with hexane and the title compound isolated as a white solid (0.58 g, 83%).

Example 16
(R)-6,6'-Dicyano-2,2'-dibenzoxy-1,1'-binaphthyl

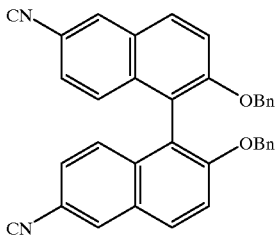

A solution of (R)-6,6'-dibromo-2,2'-dibenzoxy-1,1'-binaphthyl (5.60 g, 8.97 mM), prepared according to Example 15, copper (I) cyanide (3.23 g, 36.0 mM) in DMF (50 ml) was stirred at 170° C. for 12 hours under an atmosphere of argon. After cooling the reaction mixture was soured onto aqueous sodium cyanide (100 ml) and the resulting mixture stirred until all the dark solids were quenched to give a pale brown slurry. The solids were collected by filtration, dissolved in dichloromethane, dried over sodium sulphate and the solvent removed in vacuo to give a brown solid. Purification by column chromatography eluting with 30% ethyl acetate:hexane gave the title compound as a white solid (3.27 g, 71%).

Example 17

(R)-6,6'-Dicarboxy-2,2'-dibenzoxy-1,1'-binaphthyl

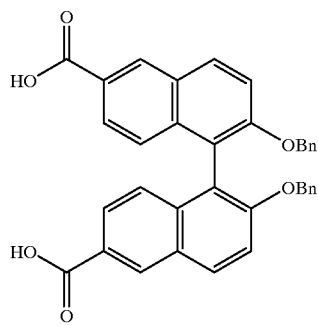

2N sodium hydroxide (100 ml) was added to a stirred solution of (R)-6,6'-dicyano-2,2'-dibenzoxy-1,1'-binaphthyl (3.27 g, 6.34 mM), prepared according to Example 16, in 2-methoxy ethanol (50 ml). The resulting reaction mixture was stirred at reflux for 24 hours after which it was cooled to room temperature and acidified with 2N HCl to pH 4. The resulting white precipitate was collected by filtration and washed with water. The white solid was then washed with acetone and the filtrate concentrated in vacuo to give the title compound as a white solid (2.35 g, 67%).

Example 18

(R)-6,6'-di-methylcarboxy-2,2'-dibenzoxy-1,1'-binaphthyl

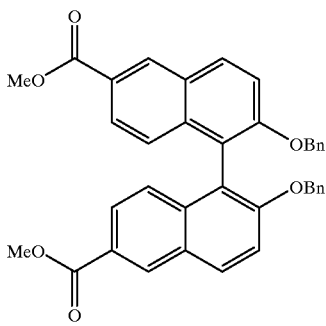

A stirred solution of (R)-6,6'-dicarboxy-2,2'-dibenzoxy-1,1'-binaphthyl (2.35 g, 4.24 mM), prepared according to Example 17, methyl iodide (1.1 ml, 17.0 mM) and potassium carbonate (2.93 g, 21.2 mM) in anhydrous acetone (50 ml) was refluxed under argon for 16 hours. After cooling to room temperature the solvent was removed in vacuo. The residue was dissolved in dichloromethane (50 ml) and water (50 ml). The layers were separated and the aqueous layer washed with dichloromethane (2×50 ml). The combined organic layers were dried over sodium sulphate and concentrated in vacuo to give a pale yellow oil. Purification by column chromatography eluting with 10% ethyl acetate:hexane yielded the title compound as an off-white solid (2.39 g, 97%).

Example 19

(R)-6,6'-di-methylcarboxy-1,1'-bi-2-naphthol

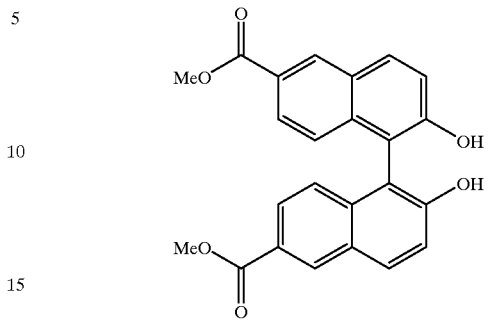

10% Palladium on carbon (1.0 g) was added under an atmosphere of argon to a degassed stirred solution of (R)-6,6'-di-methylcarboxy-2,2'-dibenzoxy-1,1'-binaphthyl (2.35 g, 4.04 mM), prepared according to Example 18, in ethyl acetate (40 ml) and methanol (40 ml). The resulting suspension was stirred under an atmosphere of hydrogen at atmospheric pressure for 16 hours. The reaction mixture was filtered through a pad of celite and the solid washed with ethyl acetate (3×20 ml). The solvent was removed in vacuo to give a white solid (1.62 g, 99%) which required no further purification.

Example 20

(R)-6,6'-di-methylcarboxy-2,2'-di-trifluoromethanesulphonate-1,1'-binaphthyl

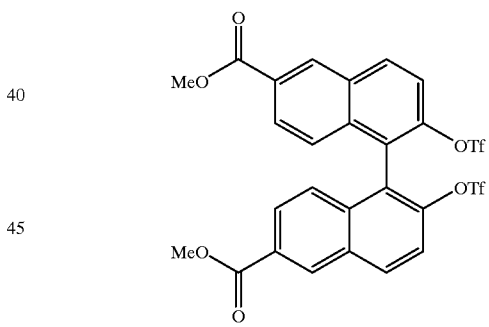

Trifluoromethanesulphonic anhydride (70 mg, 0.25 mM) was added to a stirred solution of (R)-6,6'-di-methylcarboxy-1,1'-bi-2-naphthol (40 mg, 0.095 mM), prepared according to Example 19, 4-dimethylaminopyridine (5 mg) and 2,6-lutidine (28 mg, 0.26 mM) in dichloromethane (5 ml) at 0° C. under an atmosphere of argon. The reaction mixture was allowed to warm to room temperature and stirred for a further 16 hours. Saturated sodium bicarbonate solution (10 ml) was added to the reaction mixture to quench and the organic layer separated. The aqueous phase was washed successively with dichloromethane (2×10 ml). The combined organic extracts were dried over sodium sulphate and the solvent removed in vacuo to give an oil. Purification by column chromatography eluting with 30% ethyl acetate-:hexane gave the title compound as a pale brown solid (60 mg, 91%).

Example 21
(R)-6,6'-di-methylcarboxy-2,2'-bis(diphenylphosphino)-1,1'-binaphthyl

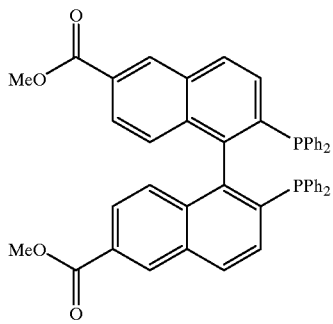

A solution of NiCl₂dppe (95 mg, 0.18 mM) in anhydrous dimethylformamide (1 ml) was degassed thoroughly using 7 pump/argon cycles. Diphenylphosphine (56 mg, 0.15 ml) was added and the red mixture aged at 100° C. for 1 hour. In a separate flask were degassed (R)-6,6'-di-methylcarboxy-2,2'-di-trifluoromethanesulphonate-1,1'-binaphthyl (100 mg, 0.15 mM), prepared according to Example 20, and 1,4-diazabicyclo[2.2.2]octane (67 mg, 0.60 mM) in dimethylformamide (1 ml) and added to the nickel solution via canula. The resulting deep green solution was heated at 100° C., a further portion of diphenylphosphine (56 mg, 0.15 ml) added after 4 hours and continued heating for a further 16 hours. After cooling to room temperature the mixture was diluted with ethyl acetate (5 ml), poured onto 50 ml aqueous sodium cyanide (74 mg, 1.5 mM) and stirred vigorously for 1 hour. The layers were separated and the organic phase washed with water (3×5 ml), dried over anhydrous sodium carbonate and the solvents removed in vacuo. The resulting brown solid was then dissolved in anhydrous toluene (5 ml), treated with trichlorosilane (0.5 ml) and heated at reflux for 18 hr. The mixture was quenched by pouring carefully onto 2.0 M aqueous sodium hydroxide (5 ml) and stirring vigorously for 30 mins. The layers were separated and the aqueous phase extracted with dichloromethane (3×5 ml). The combined organic layers were dried over anhydrous sodium carbonate and the solvent removed in vacuo. Purification was affected by flash column chromatography (silica gel, ethyl acetate-hexane, 20%) to give the title compound as an off-white solid (67 mg, 58%).

Example 22
(R)-6,6'-di-carboxy-2,2'bis(diphenylphosphino)-1,1'-binaphthyl

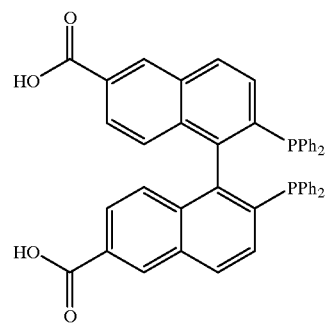

To a solution of (R)-6,6'-di-methylcarboxy-2,2'-bis(diphenylphosphino)-1,1'-binaphthyl (0.57 g, 0.74 mM), prepared according to Example 21, in tetrahydrofuran (5 ml) was added 15 ml aqueous lithium hydroxide (0.1 g, 4.2 mM) and the mixture heated at reflux for 20 hr. After cooling to room temperature the solution was acidified to pH 3 with 2.0 M aqueous HCl and extracted with ethyl acetate (3×10 ml). The combined organic extracts were dried over anhydrous sodium carbonate and the solvent removed in vacuo. Recrystallisation from methanol afforded the title compound as a white solid (0.53 g, 97%).

Example 23
(R)-6,6'-Di-(3-thienyl)-1,1'-bi-2-naphthol

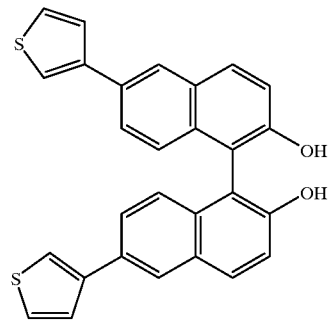

A solution of (R)-6,6'-dibromo-1,1'-bi-2-naphthol (4.0 g, 9.01 mM), prepared according to the literature procedure in J. Am. Chem. Soc. 1979, 101, 3035–3042, and tetrakis(triphenylphosphine)palladium (O) (476 mg, 0.41 mM) in ethylene glycol dimethyl ether (DME) (40 ml) was stirred under an atmosphere of argon at room temperature for 10 minutes. To the mixture was added a solution of thiophene-3-boronic acid (2.65 g, 20.7 mM) in ethylene glycol dimethly ether (20 ml), followed by aqueous 0.2 M sodium carbonate (10 ml). The mixture was refluxed under an atmosphere of argon for 12 hours. After cooling the mixture was poured into ice/water (50 ml), dichloromethane (50 ml) added and the organic layer separated. The organic layer was washed with ammonium acetate (2×25 ml), dried over sodium sulphate and the solvent removed in vacuo. Purification by column chromatography eluting with 10% ethyl acetate:hexane gave (R)-6,6'-di-(3-thienyl)-1,1'-bi-2-naphthol as a white solid (3.3 g, 81%).

Example 24
(R)-6,6'-di-(3-thienyl)-2,2'-di-trifluoromethanesulphonate-1,1'-binaphthyl

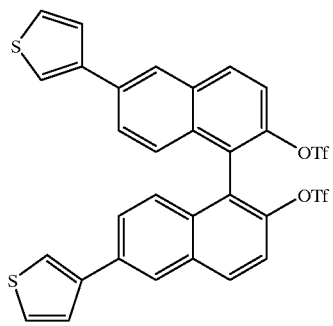

Trifluoromethanesulphonic anhydride (1.2 ml, 7.4 mM) was added to a stirred solution of (R)-6,6'-di-(3-thienyl)-1,1'-bi-2-naphthol (3.31 g, 7.4 mM), 4-dimethylaminopyridine (13 mg, 0.1 mM), prepared according to Example 23, and 2,6-lutidine (2.2 ml, 18.5 mM) in dichloromethane (30 ml) at 0° C. under an atmosphere of argon. The reaction mixture was allowed to warm to room temperature and stirred for a further 5 hours. Saturated sodium bicarbonate solution (20 ml) was added to the reaction mixture to quench and the organic layer separated. The aqueous phase was washed successively with dichloromethane (2×30 ml). The combined organic extracts were dried over sodium sulphate and the solvent removed in vacuo to give an oil. Purification by column chromatography eluting with 5% ethyl acetate:hexane gave the title compound as a colourless oil (4.2 g, 79%).

Example 25

(R)-6,6'-di-(3-thienyl)-2,2'-bis(diphenylphosphino)-1,1'-binaphthyl

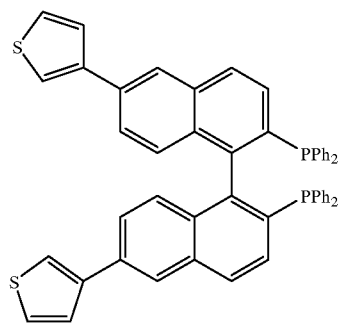

A solution of NiCl$_2$dppe (1.8 g, 4.79 mM) in anhydrous dimethylformamide (15 ml) was degassed thoroughly using 7 pump/argon cycles. Diphenylphosphine (1.1 ml, 2.95 mM) was added and the red mixture aged at 100° C. for 1 hour. In a separate flask were degassed (R)-6,6'-di-(3-thienyl)-2,2'-di-trifluoromethanesulphonate-1,1'-binaphthyl (2.1 g, 2.94 mM), prepared according to Example 24, and 1,4-diazabicylco[2.2.2]octane (1.32 g, 11.74 mM) in dimethylformamide (15 ml) and added to the nickel solution via canula. The resulting deep green solution was heated at 100° C., a further portion of diphenylphosphine (1.1 ml, 2.95 mM) added after 4 hours and continued heating for a further 16 hours. After cooling to room temperature the mixture was diluted with ethyl acetate (50 ml), poured onto 50 ml aqueous sodium cyanide (1.4 g, 29.2 mM) and stirred vigorously for 1 hour. The layers were separated and the organic phase washed with water (3×25 ml), dried over anhydrous sodium sulphate and the solvents removed in vacuo. The resulting brown solid was then dissolved in anhydrous toluene (50 ml), treated with trichlorosilane (9.9 ml, 1.18 mM) and heated at reflux for 18 hours. The mixture was quenched by pouring carefully onto 2.0 M aqueous sodium hydroxide (50 ml) and stirring vigorously for 30 minutes. The layers were separated and the aqueous phase extracted with dichloromethane (3×50 ml). The combined organic layers were dried over anhydrous sodium carbonate and the solvent removed in vacuo. Purification was effected by flash column chromatography (silica gel, ethyl acetate-hexane, 5%) to give the title compound as a white solid (1.1 g, 48%).

Example 26
(R)-6,6'-di-phenyl-1,1'-bi-2-naphthol

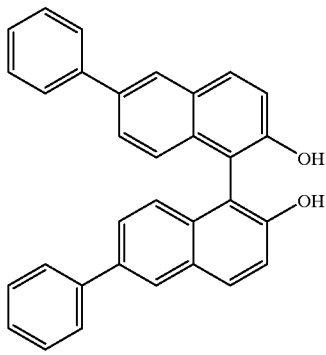

A solution of (R)-6,6'-dibromo-1,1'-bi-2-naphthol (3.07 g, 6.92 mM), prepared according to the literature procedure in J. Am. Chem. Soc. 1979, 101, 3035–3042, and tetrakis(triphenylphosphine)-palladium (O) (0.80 g, 0.69 mM) in anhydrous toluene (30 ml) was stirred under an atmosphere of argon at room temperature. To the mixture was added dropwise phenyltrimethyl tin (5.0 g, 20.7 mM). The mixture was refluxed under an atmosphere of argon for 16 hours. After cooling the mixture was filtered through a pad of celite and washed with ethyl acetate (2×30 ml). The solvent was removed in vacuo to yield a yellow oil. Purification by column chromatography eluting with dichloromethane gave the title compound as an off-white solid (1.92 g, 63%).

Example 27
(R)-6,6'-di-phenyl-2,2'-di-trifluoromethanesulphonate-1,1'-binaphthyl

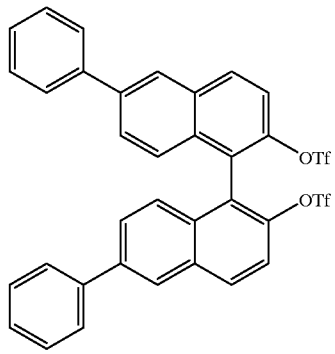

Trifluoromethanesulphonic anhydride (0.1 ml, 0.69 mM) was added to a stirred solution of (R)-6,6'-di-phenyl-1,1'-bi-2-naphthol (0.27 g, 0.62 mM), prepared according to Example 26, 4-dimethylamino-pyridine (2.3 mg, 0.009 mM) and 2,6-lutidine (0.2 ml, 1.6 mM) in dichloromethane (5 ml) at 0° C. under an atmosphere of argon. The reaction mixture was allowed to warm to room temperature and stirred for a further 16 hours. Saturated sodium bicarbonate solution (10 ml) was added to the reaction mixture to quench and the organic layer separated. The aqueous phase was washed successively with dichloromethane (2×10 ml). The combined organic extracts were dried over sodium sulphate and the solvent removed in vacuo to give an oil. Purification by column chromatography eluting with 2% ethyl acetate:hexane gave the title compound as a colourless oil (0.36 g, 85%).

Example 28
(R)-6,6'-di-phenyl-2,2'-bis(diphenyl-phosphino)-1,1'-binaphthyl

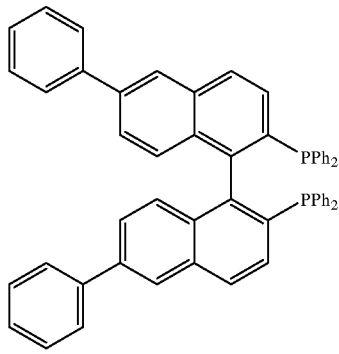

A solution of NiCl$_2$dppe (1.98 g, 3.74 mM) in anhydrous dimethylformamide (10 ml) was degassed thoroughly using 7 pump/argon cycles. Diphenylphosphine (1.1 ml, 3.12 mM) was added and the red mixture aged at 100° C. for 1 hour. In a separate flask were degassed (R)-6,6'-di-phenyl-2,2'-di-trifluoromethanesulphonate-1,1'-binaphthyl (2.19 g, 3.12 mM), prepared according to Example 27, and 1,4-diazabicyclo[2.2.2]octane (1.40 g, 12.5 mM) in dimethylformamide (10 ml) and added to the nickel solution via canula. The resulting deep green solution was heated at 100° C., a further portion of diphenylphosphine (1.1 ml, 3.12 mM) added after 4 hours and continued heating for a further 16 hours. After cooling to room temperature the mixture was diluted with ethyl acetate (50 ml), poured onto 50 ml aqueous sodium cyanide (1.53 g, 31.2 mM) and stirred vigorously for 1 hour. The layers were separated and the organic phase washed with water (3×30 ml), dried over anhydrous sodium carbonate and the solvents removed in vacuo. The resulting brown solid was then dissolved in anhydrous toluene (50 ml), treated with trichlorosilane (9.0 ml, 1.1 mM) and heated at reflux for 18 hr. The mixture was quenched by pouring carefully onto 2.0 M aqueous sodium hydroxide (50 ml) and stirring vigorously for 30 mins. The layers were separated and the aqueous phase extracted with Dichloromethane(3×50 ml). The combined organic layers were dried over anhydrous sodium carbonate and the solvent removed in vacuo. Purification was affected by flash column chromatography (silica gel, ethyl acetate-hexane, 5%) to give the title compound as a white solid (1.30 g, 54%).

Example 29
(R)-6,6'-hydroxymethyl-2,2'-dimethoxy-1,1'-binaphthyl

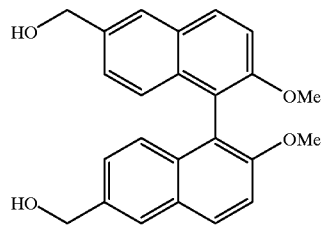

To a stirred solution of (R)-6,6'-dibromo-2,2'-dimethoxy-1,1'-binaphthyl (0.5 g, 1.06 mM) in tetrahydrofuran (5 ml) at −78° C. under an atmosphere of argon was added n-butyl lithium (1.7 ml, 4.24 mM). The reaction mixture was warmed to 0° C. and the cooled back down to −78° C. To the reaction mixture was added a suspension of paraformaldehyde (0.20 g) in tetrahydrofuran (2 ml). The resulting reaction mixture was allowed to warm to room temperature and stirred for a further 0.5 hours after which water (5 ml) was added dropwise to quench. Ethyl acetate (10 ml) was added to the reaction mixture and the organic layer separated. The aqueous phase was washed with ethyl acetate (2×10 ml). The combined organic layers were dried over sodium sulphate and the solvent removed in vacuo. Purification by column chromatography eluting with 20% ethyl acetate:hexane gave the title compound as a white solid (0.27 g, 68%).

Modifications of the 6,6'-methyl alcohol functionalities may now be carried out prior to transformation to the corresponding BINAPs, analogously to Examples 6 to 8, to give further compounds of the invention.

Example 30
(R)-6,6'-dicarbaldehyde-2,2-dimethoxy-1,1'-binaphthyl

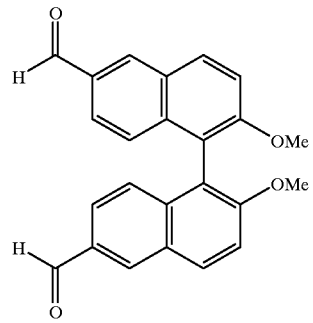

To a stirred solution of (R)-6,6'-dibromo-2,2'-dimethoxy-1,1'-binaphthyl (0.5 g, 1.06 mM) in tetrahydrofuran (5 ml) at −78° C. under an atmosphere of argon was added n-butyl lithium (1.7 ml, 4.24 mM). The reaction mixture was warmed to 0° C. and then cooled back down to −78° C. The reaction mixture was added via cannula to a cooled (−78° C.) stirred solution of dimethylformamide (1 ml) under an atmosphere of argon. The resulting reaction mixture was allowed to warm to room temperature and stirred for a further 2 hours after which water (5 ml) was added dropwise to quench. Ethyl acetate (10 ml) was added to the reaction mixture and the organic layer separated. The aqueous phase was washed with ethyl acetate (2×10 ml). The combined organic layers were dried over sodium sulphate and the solvent removed in vacuo. Purification by column chromatography eluting with 10% ethyl acetate:hexane gave the title compound as a white solid (0.21 g, 54%).

Modifications of the 6,6'-aldehyde functionalities may now be carried out prior to transformation to the corresponding BINAPs, analogously to Examples 6 to 8, to give further compounds of the invention.

Example 31
4-(6-(R)-2,2'-dimethoxy-1,1'-binaphthyl)-butanoic acid

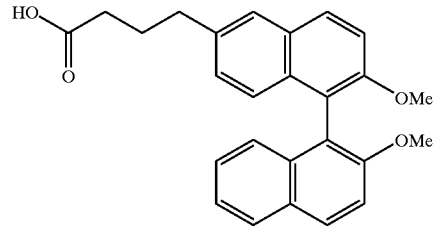

A solution of 4-(6-(R)-2,2'-dimethoxy-1,1'-binaphthyl) ethylbutanoate (5) (210 mg, 0.49 mM) and 2N sodium hydroxide (13 ml) in THF (5 ml) was stirred at reflux for 15 hours. After cooling the reaction mixture was acidified to pH 4 by the addition of 2N HCl. The mixture was extracted with dichloromethane (3×20 ml). The combined organic layers were dried over sodium sulphate and the solvent removed in vacuo. Purification by column chromatography eluting with 40% ethyl acetate:hexane gave the title compound as a white solid in a yield of 180 mg (92%).

Example 32

(R)-6,5-(1,2-cyclohexan-3-one)-1,1'-bi-2-naphthol

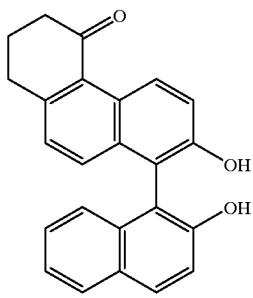

To a pre-cooled (−78° C.) stirred, mixture of 4-(R)-(6)-2,2'-dimethoxy-1,1'-binaphthyl)-butanoic acid, prepared according to Example 31, (3.1 g, 7.24 mM) in dichloromethane (30 ml) under argon was added BBr3 (1.35 ml, 14.48 mM) dropwise. The reaction mixture was allowed to warm to room temperature and stirred for 2 hours. The reaction mixture was quenched by the dropwise addition of water (20 ml) and the resulting mixture extracted with dichloromethane (2×25 ml). The combined organic extracts were dried over sodium sulphate, filtered and the solvent removed in vacuo. Purification by column chromatography eluting with 10% ethyl acetate:hexane gave the title compound as an off-white solid (1.6 g, 57%).

Example 33

(R)-6,5-(1,2-cyclohexane-3-one)-2,2'-bis(diphenylphosphino)-1,1'-binaphthyl

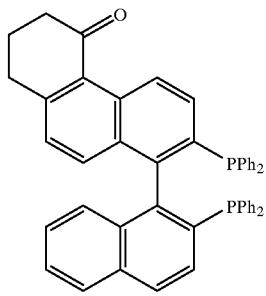

To a stirred solution of (R)-6,5-(1,2-cyclohexane-3-one)-1,1'-bi-2-naphthol (1.0 g, 2.8 mM), prepared according to Example 32, 2,6-lutidine (0.8 ml, 7.0 mM) and 4-dimethyl aminopyridine (6 mg, 0.04 mM) in dichloromethane (20 ml) at 0° C. under an atmosphere of argon was added dropwise triflic anhydride (1.5 ml, 8.4 mM). The resulting reaction mixture was warmed to room temperature and stirred under argon for 5 hours. Water (20 ml) was added to the reaction mixture to quench it and the organic layer was separated. The aqueous layer was washed with dichloromethane (2×20 ml). The combined organic layers were dried over sodium sulphate and concentrated in vacuo. Purification by column chromatography eluting with 15% ethyl acetate:hexane gave the ditriflate of the starting material as an off-white solid (1.52 g, 87%).

To a stirred, degassed solution of NiCl2dppe (870 mg, 1.62 mM) in anhydrous DMF (5 ml) under argon was added diphenylphosphine (1.0 ml, 2.73 mM). The resulting red mixture was stirred at 100° C. for 1 hour. To this mixture at 100° C. was added a degassed solution of the above triflate (0.9 g, 1.45 mM) and 1,4-diazabicyclo[2.2.2]octane (0.59 g, 5.54 mM) in dimethylformamide (DMF) (10 ml) via cannula. The resulting dark green solution was heated at 100° C. for 4 hours after which a further portion of diphenylphosphine (1.0 ml, 2.73 mM) was added. Heating was continued for a further 16 hours. After cooling the mixture was diluted with ethyl acetate (25 ml), poured into 25 ml aqueous sodium cyanide (0.68 g, 13.6 mM) and stirred vigorously for 1 hour. The layers were separated and the organic layer washed with water (3×15 ml), dried over sodium sulphate and the solvents removed in vacuo. The resulting solid was dissolved in toluene (20 ml), treated with trichlorosilane (4.26 ml, 0.59 mM) and heated at reflux for 18 hours. The mixture was quenched by the careful addition of 2N aqueous sodium hydroxide (40 ml) and stirring vigorously for 30 mins. The layers were separated and the aqueous phase extracted with dichloromethane (3×20 ml). The combined organic layers were dried over sodium sulphate and the solvent removed in vacuo. Purification by column chromatography eluting with 10% ethyl acetate:hexane gave (R)-6,5-(1,2-cyclohexane-3-one)-2,2'-bis(diphenylphosphino)-1,1'-binaphthyl as a white solid (0.54 g, 51%).

Example 34

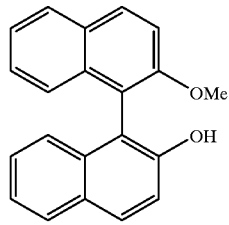

(R)-DimethoxyBINOL (3) (9046 g, 1 mole equivalent), prepared according to Example 1, in dichloromethane (10 vol) was cooled to −70° C. Boron tribromide (1.05 mole eq.) was added dropwise whilst maintaining the temperature at <−70° C. The reaction mixture was stirred at this temperature until no starting material remained (typically 2 hours, TLC:DCM). On reaction completion methanol (0.3 vol) was added dropwise, again maintaining the temperature at <−70° C. The reaction mixture was allowed to warm to 0° C., when water (6 vol) was added and the resulting mixture stirred for 30 minutes. The layers were separated and the aqueous layer was washed with DCM (2×1 vol). The organic extracts were combined, washed with sat. aq. sodium bicarbonate (3 vol) and dried over magnesium sulphate. Filtration, followed by concentration at reduced pressure and drying in a vacuum oven overnight at 40° C. gave the product as a white solid in 99% overall yield (8541 g).

(In Examples 34–42, 1 volume corresponds to 1 liter of solvent per kilogram of substrate.)

Example 35

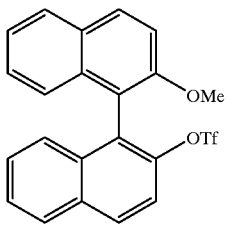

2,6-Lutidine (1.4 mole eq.) was added dropwise to a mixture of the mono-methoxy-BINOL derivative prepared according to Example 34 (8541 g, 1 mole eq.) and DMAP (5 mole %) in DCM (10 vol.), whilst maintaining the temperature in the range 0–5° C. Triflic anhydride (1.2 mole eq.) was then introduced dropwise, again keeping the temperature in the range of 0–5° C. The resulting mixture was allowed to warm to room temperature and stirred overnight, after which time the reaction was complete (TLC:DCM). Water (5 vol.) was added and the reaction mixture stirred for 10 minutes. The layers were separated and the aqueous layer washed with DCM (2×1 vol.). The combined organic extracts were washed with 2M hydrochloric acid (3 vol.), water (3 vol.). sat. aq. sodium bicarbonate (3 vol.) and dried over magnesium sulphate. Filtration, followed by concentration of the filtrate at reduced pressure gave a purple oil. Isopropyl alcohol (2 vol.) was introduced to the oil and the flask warmed at 40° C. on a rotary evaporator until a yellow solution was obtained. The alcoholic solution was allowed to cool to room temperature and then cooled in ice. The resulting yellow solid was removed by filtration and washed with ice-cooled isopropyl alcohol (1×0.5 vol.). After drying in a vacuum oven overnight at 40° C. the desired product was obtained as a pale yellow solid in 88% overall yield (10715 g).

Example 36

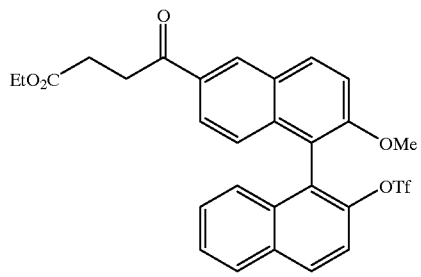

Aluminium chloride (2 mole eq.) was added portionwise to a solution of ethyl succinyl chloride (2 mole eq.) in DCE (6.5 vol.), whilst maintaining the temperature in the range 0–10° C. The resulting mixture was stirred until all the aluminium chloride had dissolved. To the resulting solution, a mixture of the mono-triflate BINOL derivative produced according to Example 35 (10751 g, 1 mole eq.) in DCE (2 vol.) was added dropwise whilst maintaining the temperature in the range 0–5° C. The cooling bath was removed and the reaction mixture stirred at room temperature overnight. The brown solution was warmed to 70° C. and monitored every 10 minutes by TLC (30% ethyl acetate in hexanes) until the reaction was complete (typically 1 hour). The reaction mixture was allowed to cool to room temperature and then added dropwise, with care, onto ice water (8 vol.). The resulting mixture was stirred at room temperature for 30 minutes. The layers were separated and the aqueous layer washed with DCM (3×1 vol.). The combined organic extracts were washed with water (4 vol.) and sat. aq. sodium bicarbonate (4 vol.). Filtration, followed by concentration at reduced pressure to 5 volumes gave a dark brown solution. This solution was heated at 40° C. for 1 hour with decolourising charcoal (0.25 wt) and hot filtered through glass fibre pads (this was necessary in order to obtain a solid product in the following reaction step). The charcoal was washed with DCM until all the product was reisolated. Concentration at reduced pressure gave a brown oil which was taken directly into the next step of the reaction (see Example 37).

Example 37

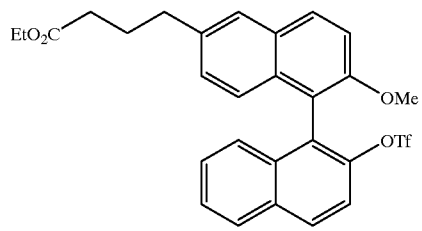

The crude product from Example 36 (1 mole eq.) was dissolved in trifluoroacetic acid (3 vol.) and cooled to <5° C. Triethylsilane (4 mole eq.) was added at such a rate so as to maintain the temperature at <30° C. The resulting mixture was stirred at room temperature until no starting material remained (typically 2 hrs; TLC: 30% ethyl acetate in hexanes). Dichloromethane (3 vol.) was then added to the reaction mixture and the resulting solution added dropwise to ice/water (3 vol.). The layers were separated and the aqueous layer washed with DCM (2×1 vol.). The organic extracts were combined and washed with water (2×3 vol.), sat. aq. sodium bicarbonate (3 vol.), water (3 vol.) and dried over magnesium sulphate. Concentration at reduced pressure gave a brown oil to which was added isopropyl alcohol (1 vol.) and the resulting mixture stirred overnight at room temperature. The resulting yellow solid was isolated by filtration and recrystallised from boiling isopropyl alcohol (1 vol.). After drying the yellow solid thus obtained in a vacuum oven at 40° C. overnight, the desired product was obtained in 63% overall yield (8617 g) over two stages.

Example 38

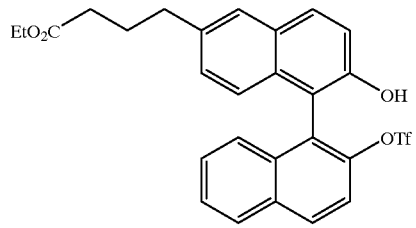

A solution of the product from Example 37 (8617 g, 1 mole ea.) in dichloromethane (10 vol.) was cooled to −20° C. Boron tribromide (2 mole eq.) was added dropwise maintaining the temperature at <−20° C. The reaction mixture was stirred at this temperature until no starting material remained (typically 2 hours, TLC:DCM) On reaction completion methanol (3 vol.) was added dropwise, again maintaining the temperature at <−20° C. The reaction mixture was allowed to warm to >0° C. when water (6 vol.) was added and the resulting mixture stirred for 30 minutes. The layers were separated and the aqueous layer washed with DCM (2×1 vol.). The organic extracts were combined, washed with sat. aq. sodium bicarbonate (3 vol.) and dried over magnesium sulphate. Filtration, followed by concentration at reduced pressure gave the crude product as a pale brown oil. A 4L sinter funnel was slurry packed with silica, 1.9 kg, in DCM and sucked dry. The crude reaction mixture (500 g) was dissolved in DCM (700 ml) and loaded onto the top of the column. The product was separated from baseline material by eluting with DCM (10×2L). Concentration at reduced pressure gave the pure product as a brown oil in 90% overall yield (7539 g)

Example 39

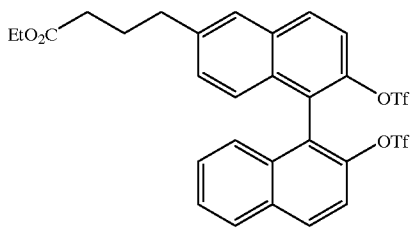

2,6-Lutidine (1.4 mole eq.) was added dropwise to a mixture of the mono-methoxy-BINOL product from Example 38 (7539 g, 1 mole eq.) and DMAP (5 mole %) in DCM (10 vol.), whilst maintaining the temperature in the range 0–5° C. Triflic anhydride (1.2 mole eq.) was then introduced dropwise again keeping the temperature in the range of 0–5° C. The resulting mixture was allowed to warm to room temperature and stirred overnight, after which time the reaction was complete (TLC:DCM). Water (5 vol.) was added and the reaction mixture stirred for 10 minutes. The layers were separated and the aqueous layer washed with DCM (2×1 vol.). The combined organic extracts were washed with 2M hydrochloric acid (3 vol.), water (3 vol.), sat. aq. sodium bicarbonate (3 vol.) and dried over magnesium sulphate. Filtration, followed by concentration of the filtrate at reduced pressure gave a brown oil in 98% overall yield (9319 g), which was taken directly to the next stage without further purification.

Example 40

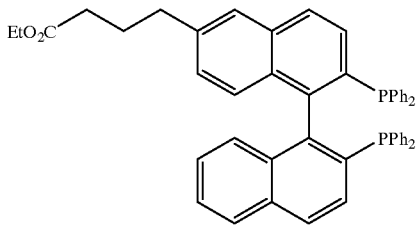

To a stirred suspension of NiCl$_2$dppe (0.2 mole eq.) in DMF (3 vol.) was added a 50% solution of diphenylphosphine in DMF (0.56 mole eq. of diphenylphosphine) and the mixture heated to 100° C. After 45 minutes at this temperature a solution of the ditriflate product form Example 39 (5843 g, 1 mole eq.) and DABCO (4 mole eq.) in DMF (5 vol.) was added. After a further 1.3 and 6 hours at 100° C., additional portions of the diphenylphosphine solution (0.56 mole eq. of diphenylphosphine) were added and the resulting mixture stirred at 100° C. overnight. Once the reaction was complete (TLC 20% ethyl acetate in hexanes) the reaction mixture was allowed to cool to room temperature and poured carefully onto vigorously stirred ice/water (10 vol.). Stirring was maintained for 30 minutes and the precipitated solids collected by filtration), washed with water (4×2 vol.) and sucked dry. The residual solids were then dissolved in DCM (5 vol.) and the solution left to stand overnight. Any water was separated and the organic solution filtered through Celite. After drying the solution over magnesium sulphate, concentration at reduced pressure gave a brown oil. Purification of the crude oil was achieved by flash column chromatography. A 4L sinter funnel was packed with silica (1.8 kg) in DCM and sucked dry. The crude reaction mixture (250 g) was dissolved in DCM (500 ml) and loaded onto the column. Eluting with: 5% ethyl acetate in hexanes (5×2L) isolated an unidentified impurity (R$_f$ 0.75), eluting with 20% ethyl acetate in hexanes (7×2L) gave the desired product (R$_f$ 0.57) and eluting with 50% ethyl acetate in hexanes (5×2L) gave the phosphine oxides (R$_f$ 0.1). Concentration at reduced pressure gave the desired product in 66% overall yield (4291 g), as a yellow solid, and the phosphine oxides (mono and di-mixture), 1.3 Kg overall as a brown oil.

Example 41

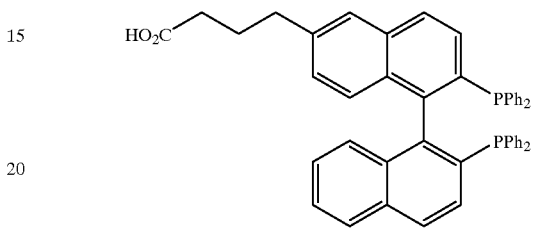

To a solution of the BINAP ester product from Example 40 (4571 g, 1 mole eq.) in THF (6 vol.) was added lithium hydroxide (2 mole eq.) in water (3 vol.) and the mixture heated at reflux overnight. Once the reaction was complete, (TLC: 50% ethyl acetate in hexanes), it was allowed to cool to room temperature and conc. hydrochloric acid added until the pH=1. Dichloromethane (5 vol.) was added and the mixture stirred for 10 minutes. The layers were separated and the aqueous layer washed with DCM (2×1 vol.). The combined organic extracts were washed with water (2×2 vol.) and dried over magnesium sulphate. Filtration, and concentration at reduced pressure gave the crude product as a pale yellow oil. Addition of methanol (4 vol.) and stirring at room temperature for 2 hours yielded a white precipitate. The precipitate was isolated by filtration and recrystallised from methanol (30–35 vol.). The mother liquors were concentrated at reduced pressure and recrystallised once more to give a second crop. After drying the solids in a vacuum oven overnight at 40° C. the desired product was obtained as a white solid in 63% overall yield (2782 g).

Example 42

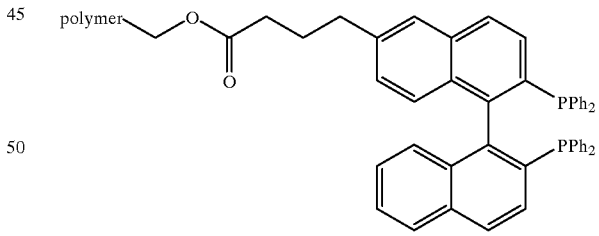

A mixture of chloromethyl-polystyrene resin (1 mole eq.), the BINAP acid product from Example 41 (2129 g, 1.1 mole eq.), caesium carbonate (2.2 mole eq.) and potassium iodide (0.5 eq.) in DMF (17 vol.) was heated at 80° C. for 60 hours. The reaction mixture was allowed to cool to 50° C. and filtered through a sinter funnel. The residual solids were washed in the sinter funnel with DMF (1 vol.) and water at 40° C. (2×2 vol.). The remaining solids were then repeatedly slurried in water at 40° C. (2 vol.) until the pH of the filtrate was neutral. The solids were then slurried with THF (8 vol.), MeOH (2×5 vol.) and dried in the vacuum oven at 40° C. overnight to give the desired polymer bound BINAP as an off-white powder (5190 g). Loadings ranged from 0.32–0.45 mmol/g.

Example 43
Analysis of Hydrogenation Products

[Structure: pentane-2,4-dione methyl ester reacting with (11) or (12), H₂, THF, MeOH, 10 atm, 50° C., 20 hours → methyl 3-hydroxypentanoate (OH, OMe)]

[Structure of (11), (12): R⁴O-substituted binaphthyl with PPh₂ groups]

| Catalyst | R⁴ | Optical purity of product | Yield |
|---|---|---|---|
| (11) (R-enantiomer) | CH₃CH₂ | 98.9% | 100% |
| (12) (R-enantiomer) | H | 98.8% | 100% |
| (R)-BINAP-RuBr₂ [1] | | 99% | 100% |

[1]Comparative Example - literature values taken from Genet, J. P., Pinel, C., Ratovelomanana-Vidal, V., Mallart, S., Pfister, X., Bischoff, L., Cano de Andrade, M. C., Darses, S., Galopin, C., Laffitte, J. A., Tet. Asymm., 1994, 5(4), 675.

The non $C_2$-symmetric catalysts of the invention show very similar yields and essentially identical enantiomeric excesses to the prior art catalyst.

Example 44
Some Typical Values Demonstrating the Comparison of Support-bound Catalysts According to the Invention with Prior Art Catalysts

| Solution phase BINAP catalysts (typical values)[2] | Support-bound BINAP catalysts of the invention |
|---|---|
| 1–2 mol % catalyst used | 2 mol % catalyst used |
| 4–20 atm. hydrogen used | 10 atm. hydrogen used |
| 40–80° C. temperature used | 35–50° C. temperature used |
| 30 min–16 hours reaction time | 16–24 hours reaction time (36 hours when reusing catalyst for second time) |
| 70–100% purities | 80–100% purities, 100% conversions |
| 75–>99% optical purity | 64–<96.9% optical purity |

[2]Values for the solution phase BINAP were taken from Genet, J.P., Pinel, C., Ratovelomanana-Vidal, V., Mallart, S., Pfister, X., Bischoff, L., Cano De Andrade, M.C., Darses, S., Galopin, C., Laffitte, J.A., Tet. Asymm., 1994, 5(4), 675.

It can be seen from the above values that the support-bound catalysts of the invention can be used under very similar conditions to the prior art catalysts, and with similar results.

Example 45
Comparison of Support Bound Catalyst of the Invention with Prior Art Catalyst

| Substrate | Conditions and results using support bound catalyst (10) of the invention (2 mol %) | Comparative conditions and results using prior art solution phase (R) or (S) - BINAP-RuBr₂ catalyst (2 mol %)[3] |
|---|---|---|
| 13 | THF:MeOH (1:1), 10 atm., 50° C., 18 hours, 100% conv., 96.9% ee | MeOH, 20 atm., 40° C., 16 hours, 100% yield, >99% ee |
| 14 | THF, trace MeOH, 10 atm., 35° C., 23 hours, 100% conv. 64.5% ee | THF:EtOH (1:1), 20 atm., 48–72 hours, 1 mol % catalyst, 70% yield, 75% ee |
| 15 | THF:EtOH (1:1), 10 atm., 50° C., 24 hours, 100% conv., 94.9% ee | EtOH, 70 atm., 1 hours, 93° C., 100% yield, 89% ee |
| 16 | THF, trace MeOH, 10 atm., 35° C., 23 hours, 100% conv. 68% ee | N/A |
| 17 | THF:MeOH (1:1), 10 atm., 50° C., 20 hours, 100% conv.* 89% ee | MeOH, 4 atm., 80° C., 25 min, 95% yield,*** 99% ee |
| 18 | THF:MeOH (1:1), 10 atm., 50° C., 20 hours, 100% conv** | MeOH, 4 atm., 20° C., 24 hours, 1 mol % catalyst,**** 100% yield, 90% ee |

*complete hydrogenation of the olefin and ketone was observed.
**50% of the corresponding methyl ester was observed.
***less than 5% of the corresponding β-hydroxyester was observed.
****(R)-BINAP-Ru(all)₂ catalyst used.
[3]Values for the solution phase BINAP were taken from Genet, J. P., Pinel, C., Ratovelomanana-Vidal, V., Mallart, S., Pfister, X., Bischoff, L., Cano De Andrade, M. C., Darses, S., Galopin, C., Laffitte, J. A., Tet. Asymm., 1994, 5(4), 675.

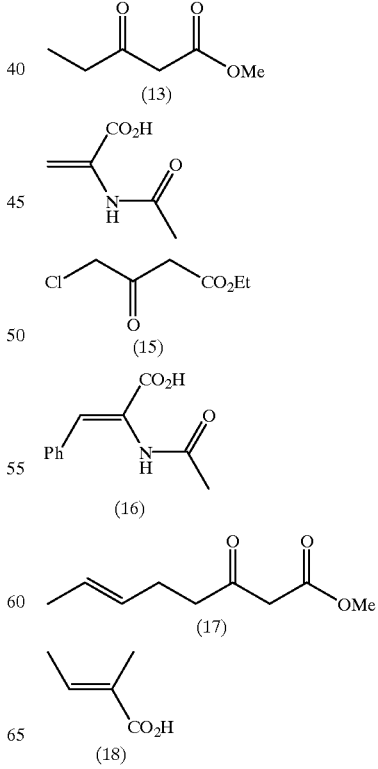

(13), (15), (16), (17), (18)

The above results demonstrate that the support-bound catalysts of the invention produce very similar results interms of yield and enantiomeric excess as do the prior art catalysts. However, work up and purification of the products is significantly easier when the catalysts of the invention are used.

What is claimed is:

1. Compounds of general formula (I)

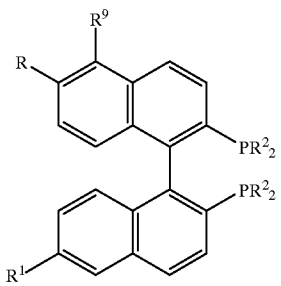

(I)

wherein

R denotes $C_{1-6}$ alkyl, $C_{1-6}$ alkenyl, $C_{1-6}$-alkynyl or phenyl, wherein the $C_{1-6}$ alkyl and phenyl groups may optionally be substituted by one or more substituents selected from the group consisting of F, Cl, Br, $NO_2$, amino, naphthalene, anthracene, biphenyl, $C_{1-6}$ alkyl, $CF_3$, CN, OH, O—$C_{1-6}$ alkyl, $CO_2H$, CHO, NHCO($C_{1-6}$ alkyl), $CO_2$($C_{1-6}$ alkyl), N($C_{1-6}$ alkyl)CO, benzyl, $C_{5-6}$ cyclic ethers and $C_{2-4}$ unsaturated hydrocarbon groups, and wherein the $C_{1-6}$ alkyl group may optionally include one or more intervening heteroatoms or aryl groups in the chain, or R denotes CN, $CO_2NHR^3$, $(CH_2)_nOR^3$, $CO_2R^3$, benzyl, or Y—X—$R^4$;

$R^1$ denotes R or H;

$R^2$ denotes phenyl, phenyl substituted by one or more $C_{1-7}$ alkyl groups, O—$C_{1-6}$ alkyl groups and/or halogen atoms, or $R^2$ denotes a $C_{3-7}$ cyclic aliphatic hydrocarbon group;

$R^9$ denotes H or together with R forms a 5, 6 or 7 membered hydrocarbon ring, optionally substituted by one or more C=O, OH or amine groups;

Y denotes a straight or branched aliphatic chain, optionally incorporating one or more aromatic hydrocarbon group(s) or ether linkages in the chain, or an aromatic hydrocarbon group;

X denotes $CH_2$, $CO_2$, O, CONH, NH, $CONR^2$, $NR^2$ or a valence bond;

$R^3$ denotes H, $C_1$–$C_{10}$ alkyl, benzyl or phenyl; and $R^4$ denotes H, $C_1$–$C_6$ alkyl, an insoluble support, or a spacer group attached to an insoluble support;

with the proviso that when $R^9$ is H and $R^1$ is R, then $R^1$ and R are not unsubstituted $C_{1-6}$ alkyl;

and all enantiomers, mixtures, including racemic mixtures, and diastereomers thereof.

2. Compounds as claimed in claim 1 wherein $R^2$ denotes phenyl;

X denotes CONH or $CO_2$;

R denotes Y—X—$R^4$;

Y denotes $(CH_2)_n$ wherein n denotes 2 to 4; and $R^1$ is identical to R.

3. Compounds as claimed in claim 1 wherein $R^2$ denotes phenyl;

R denotes Y—X—$R^4$;

$R^4$ denotes an insoluble support or a spacer group attached to an insoluble support;

X denotes CONH or $CO_2$; and

Y denotes $(CH_2)_n$ herein n denotes 2 to 4.

4. Compounds as claimed in claim 1 of formula

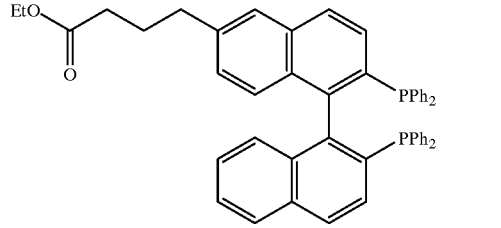

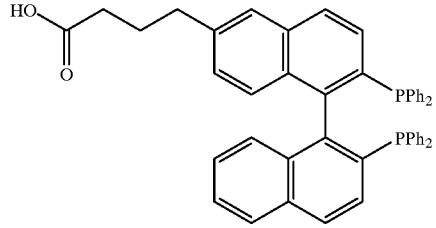

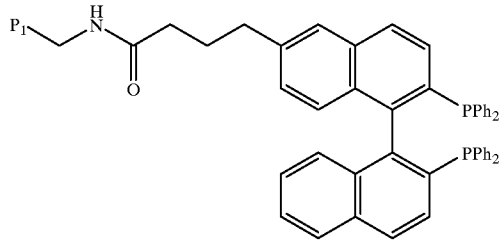

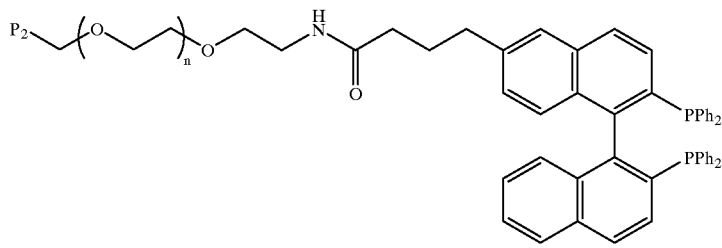

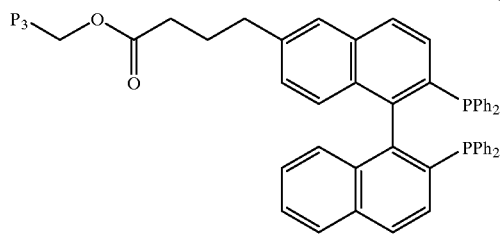

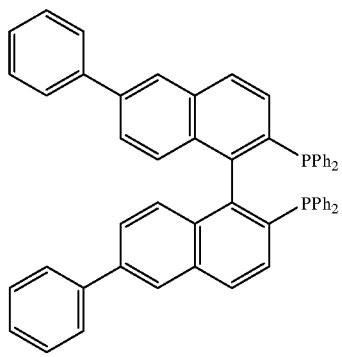

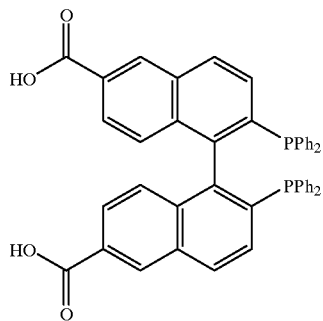

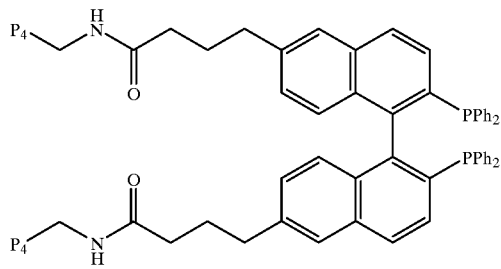

wherein:
- P$_1$ denotes aminomethyl polystyrene resin;
- P$_2$ denotes a hydroxy-terminated polyethylene glycol-g-copoly (styrene-1%-divinylbenzene) resin or a hydroxy terminated polyethylene glycol-polystyrene resin;
- P$_3$ denotes 4-hydroxymethylphenoxymethyl-copoly (styrene-1%-divinylbenzene resin, 4-alkoxylbenzyl alcohol-copoly (styrene-1%-divinylbenzene) resin or 4-alkoxybenzyl alcohol-polystyrene resin; and
- P$_4$ denotes polymer n denotes an integer from 50 to 67.

5. Compounds as claimed in claim 1 wherein the support is selected from the group consisting of polystyrene-divinyl benzene co-polymer, polystyrene resin, polyamide, aminomethylated polystyrene resin, 4-hydroxymethylphenoxymethyl-copoly(styrene-1%-divinylbenzene) resin, 4-alkoxybenzyl alcohol-copoly (styrene-1%-divinylbenzene) resin, a 4-alkoxybenzyl alcohol-polystyrene bead, aminomethylated hydroxy-terminated polyethylene glycol-g-copoly(styrene-1%-divinylbenzene) resin, aminomethylated hydroxy-terminated polyethylene glycol-polystyrene resin, polyamide-kieselguhr composites, polyhipe, cotton and paper.

6. Compounds as claimed in claim 1 which consist of a single enantiomer.

* * * * *